(12) United States Patent
Fang

(10) Patent No.: US 12,405,163 B2
(45) Date of Patent: Sep. 2, 2025

(54) HYPERSPECTRAL SENSING SYSTEM AND METHOD FOR QUALITATIVE ANALYSIS OF FLUIDS

(71) Applicant: SafeNet International LLC, Arlington Heights, IL (US)

(72) Inventor: Joseph Y. Fang, South Barrington, IL (US)

(73) Assignee: SafeNet International LLC, Arlington Heights, IL (US)

( * ) Notice: Subject to any disclaimer, the term of this patent is extended or adjusted under 35 U.S.C. 154(b) by 100 days.

(21) Appl. No.: 18/165,477

(22) Filed: Feb. 7, 2023

(65) Prior Publication Data

US 2023/0296437 A1    Sep. 21, 2023

Related U.S. Application Data

(63) Continuation-in-part of application No. 17/396,986, filed on Aug. 9, 2021, now Pat. No. 11,650,145.

(51) Int. Cl.
*G01J 3/28* (2006.01)
*G01J 3/02* (2006.01)

(52) U.S. Cl.
CPC .......... *G01J 3/2823* (2013.01); *G01J 3/0264* (2013.01); *G01J 3/0272* (2013.01); *G01J 3/0289* (2013.01); *G01J 2003/2826* (2013.01); *G01J 2003/2879* (2013.01)

(58) Field of Classification Search
CPC . G01J 2003/2826; G01J 3/2823; G01N 21/31
See application file for complete search history.

(56) References Cited

U.S. PATENT DOCUMENTS

2019/0323889 A1* 10/2019 Sano .................. G01J 3/28

OTHER PUBLICATIONS

Perkin Elmer, "The Lab Report, Episode 9: Analysis of Wear Metals in New and Used Oil", May 9, 2016 (Year: 2016).*
OriginLab Corp, "PCA for Spectroscopy App", https://www.youtube.com/watch?v=LlLreMspRbl, May 16, 2017 (Year: 2017).*
Jakob Kilgus, "Application of a Novel Low-Cost Hyperspectral Imaging Setup Operating in the Mid-Infrared Region", Nov. 30, 2018 (Year: 2018).*

* cited by examiner

*Primary Examiner* — Maurice C Smith
(74) *Attorney, Agent, or Firm* — Bishop & Diehl, Ltd.

(57) ABSTRACT

A system and method using remote sensing instrument with hyper spectrum quantitatively measure metal dust elements in lubricating oil, which includes (not limited): Al, Cd, Cr, Cu, Fe, Pb, Mg, Mn, Mo, Ni, Ag, Sn, Ti, V, Zn, B (Boron, for Coolant), Ca (Calcium for water contaminant), and particle size, cone penetration, dropping point, steel mesh oil separation, moisture, PQ concentration, in few seconds. The instrument integrates near-field communication (NFC), Internet of Thing (IoT), Cloud computing, spectral matching and other data processing, and application software forming a system to easily operated and build a model enable self-learning to improve precision through collection accumulation. With the system, the instrument as FIG. 1 can provide comprehensive on-site analysis enable preventive maintenance of mission critical engine and rotating equipment. The characteristics of the system are easy to operate, get result quickly, and self-learning to improve precision.

25 Claims, 24 Drawing Sheets

System Functional Component Flowchart

Calibration and Expert System

Processing Procedures to Build Hyperspectral Model

Processing Procedures to Calculate Test Results

Hyperspectral Models Built by Various Application Scenarios

HYPERSPECTRAL SENSING SYSTEM AND METHOD FOR QUALITATIVE ANALYSIS OF FLUIDS

RELATED APPLICATION

The present disclosure is a Continuation-In-Part (CIP) of and claims filing priority to U.S. patent application Ser. No. 17/396,986 titled "Hyperspectral Sensing System and Method For Qualitative Analysis of Fluids" and filed on Aug. 9, 2021, now U.S. Pat. No. 11,650,145. The '986 application is hereby incorporated by reference.

TECHNICAL FIELD OF INVENTION

The present invention is directed to systems, devices, and methods for using remote hyper-spectrum scanning to quantitatively measure metal dust elements in fluids, such as lubricating oil, quickly and expertly. Measurements obtained are used to determine the state of a particular oil and may include, without limitation, particle size, cone penetration, dropping point, steel mesh oil separation, moisture, and PQ concentration.

BACKGROUND OF INVENTION

Lubricant (Oil and Grease) analysis can provide critical information (i.e., a healthy condition) about a system powered by an engine. Such periodic lubricant analysis is needed in numerous industries, including the aircraft industry, the automobile and truck industry, the energy sector, wind turbines, the marine sector, mining, construction and other heavy equipment users, the agriculture industry, military, and many other government entities. A key benefit of lubricant analysis is the ability to diagnose early conditions contributing to engine fatigue and failure. Recommending and implementing preventive maintenance in response to the analysis helps avoid downtime and/or big repairs, which in turn can lead to productivity increases by limiting and scheduling downtime of running machines and vehicles.

There are various approaches to implementing a lubricant analysis program, depending on the application and maintenance objectives. These approaches commonly involve using either a conventional laboratory or on-site microlaboratory equipment. The advantage of the conventional laboratory approach is having a complete set of equipment for analysis and dedicated expert technicians to operate and interpret results. Downsides include typically long turn-around times from sample collection to delivery of a quantitative report, possible sample contamination during transport, and other mishandling issues. For at least these reasons onsite service engineers can rarely rely on laboratory reports to make real-time decisions.

Alternatively, technology has made it possible to have portable, battery-powered lubricant analysis tools with capabilities comparable to equipment used in laboratories. Such a device is disclosed in U.S. Pat. No. 9,791,386 B2 to Henning et al. (the '386 patent) and assigned to Spectro Scientific, Inc. of Chelmsford, MA (see https://www.spectrosci.com/the-latest/press-releases/fieldlab-58-portable-fluid-analysis-system-from-spectro-scientific-boosts-performance-with-new-x-ray-fluorescence-xrf-engine/). The '386 patent is hereby incorporated by reference. The '386 patent disclosed device integrates four analytical technologies, including X-Ray Fluorescence (XRF) for elemental analysis, a filter particle qualifier (FPQ) pore blockage particle counter, an infrared (IR) spectrometer, and a kinematic viscometer (40° C.). Through its four manual operations, the device can generate test results in 5-7 minutes. However, such a device typically weighs about 15 kg (about 33 pounds) and requires extensive training, if not expertise, to operate. Nonetheless, these mobile devices empower service engineers to make more informed decisions about machine and vehicle preventive maintenance.

What is needed is a system, device and method which can combine hyperspectral data processing and a Cloud-based element spectrum database to generate quantitative analysis in 3-6 seconds with laboratory-comparable results. Such an invention would give service engineers more convenient and effective maintenance-based information from a diagnosis. The inventive instrument should be capable of operation by a less skilled engineer with high throughput. Further, lubricant samples (less than 2 ml) should be repeatedly inspected, stored, and traced by the system and method.

Use of a 400 nm to 1,000 nm spectral band hyperspectral reflectance technique to quantitatively detect an amount of metal dust and chemical components in an oil, breaks with conventional emission spectrum analysis methods (atomic spectrometer technique), and significantly simplifies detection equipment, making it easily portable at about 1 kg (about 2.5 lbs). Detection is rapid, achieving acquisition of all detection results in only 3-6 seconds. Operation of the device is simple too and does not require specialized personnel. And, both operation and maintenance are inexpensive due, in part, to the use of very few consumables, with daily startup calibration requiring no consumables.

However, prior art devices and systems which use a hyperspectral reflectance technique to detect quantities of metal dust and chemical components in oil present major challenges to those of skill in the art.

For example, limited by the range of the spectral bands of the collected reflected light, the effort to identify and quantitatively detect the amounts of the metal dusts and chemical components contained in an oil sample through the existing spectral bands does not produce enough information. We can learn about a set of spectral bands corresponding to each of the detected elements, which is helpful for the separation thereof from the collected hyper-spectrum. It is also possible to establish a model according to the oil sample to be detected and the distributions of the contents of the detected components to make calculations for the oil sample to be detected and provide a statistical and inference regression algorithm. However, as a result of the interference by non-detection (random) components in an oil sample, the impact of temperature and environment on the optical components, and the impact of the operation on the instrument's structural design, detection errors might be introduced directly into the testing process. In order to make the technology of quantitative detection of oil components by hyperspectral reflectance technology practical in the application thereof, it is crucial to improve the overall accuracy of the algorithm model, the components of the device, and the structural design of the device As to prior art methods for analyzing oil components, at present atomic emission spectrometry and the Raman method are widely used by those of skill in the art. Atomic emission spectrometry is based on optical emission spectroscopy (OES) using a rotating disk electrode (RDE). The method employs a huge potential difference in discharge present between the RDE and an external rod electrode in an oil sample. This achieves vaporization and plasma conversion of the oil sample under action of an arc excitation source. The characteristic spectra corresponding to the various elements contained in the plasma-converted oil sample being tested are obtained through the excitation. The optical system of the spectrometer then collects, distinguishes, and quantifies the excited emission spectra.

An atomic emission spectrometer (AES) comprises three modules: 1) an excitation source, which applies external energy to the oil sample being tested and excites the elements in the oil sample so that they emit characteristic spectra; 2) an optical system to distinguish and identify the characteristic spectral lines corresponding to specific elements in the emission spectrum; and 3) data processing and a display, to distinguish and measure the intensity of the characteristic spectral lines of each measured element generated after beam splitting by the spectral system, and to convert the detection results into quantified results in specific units which are directly displayed to the operator.

The excitation process of the excitation source consists of causing an electric arc (or high-temperature spark) generated by the discharge to directly act on an oil sample to vaporize it and release energy. This process requires a dark chamber, and the characteristic spectrum produced by the vaporized (plasma converted) element is a three-dimensional random space (the distance from the light source to the receiving probe surface) relative to the spectrum receiving surface (probe). Using an AES, the results have an average error of about ten percent (10%), even when continuously testing an identical oil sample. Cleaning of the excitation source and oil sample dark chamber, and single-use consumables for the rotating disk electrode and the oil sample container increase cost per test.

The optical system in an atomic emission spectrometer has a detection capability that includes all spectral ranges used to characterize the spectral lines of detected elements. Since the characteristic spectral lines emitted by many elements lie outside the visible light spectrum, a spectral range of 400 nm to 2,300 nm is required for receiver identification and detection. Most light in the far-ultraviolet spectral range (i.e., 1,000 nm to 2,300 nm) will be absorbed (attenuated) when transmitted through the air. In order to collect and analyze these characteristic spectral lines in the far-ultraviolet spectral range, the optical system must be placed in a specially provided vacuum chamber. Alternatively, a special inert gas that has no absorbing effect on the ultraviolet spectrum can be injected into the optical system to ensure that the emitted characteristic spectral lines reach the optical grating system. Following refraction and diffraction, the light is projected onto a photoelectric conversion device (PMT). A sealed vacuum dark chamber, vacuum pump, and gas supply system (pressurizing pump) are consequently essential parts of a spectrometer. These components have direct implications for the volume, weight, and complexity of the spectrometer.

Due to the complexity of an atomic emission spectrometer (AES), data processing needs to perform a power-on calibration of the system daily. Calibration is done using standard oil samples of known elemental composition. Generally, three different standard oil samples are required for calibration when turning a unit on each day—as much as 40 minutes are required just to warm up the AES each time it is turned on. The equipment also requires different standard oil samples (i.e., different elemental concentrations and distributions) for standardization on a regular basis. As a result, spectral equipment relies on availability of standard oil samples, increasing the complexity of equipment operation and maintenance. In addition, because the AES must be operated in a vacuum dark chamber, the size of the instrument is massive.

Finally, an atomic emission spectrometer is only suitable for the detection of metal components. It does not have the ability to detect chemical components, flash points, viscosity, particle size, or the like, giving it a significantly limited usefulness. The following Table shows the deficiencies of comparable devices.

| Performance Comparison | Device Characteristics | Weight (Kg) | Analysis Content | | | | |
|---|---|---|---|---|---|---|---|
| | | | Metal Composition | Other* | Flash Point | Operation Time | Consumables |
| Spectroil 100 (USA) | Desktop (Lab Equipment) | 75 | Yes | No | No | 30 sec | High |
| FieldLab 58 (USA) | Portable (battery driven lasts 4 hours) | 15 | Yes | Yes | No | 5-7 min | High |
| MicroLab 40 (USA) | Desktop (Lab Equipment) | 59 | Yes | Yes | No | ~15 min | High |

*Other: Chemical composition, particle size, viscosity

Likewise, the Raman method has limitations and downsides. The Raman method uses a light source to irradiate light onto the oil. When the light refracts, a very small amount (about 1%) of the light is absorbed by the oil and changes frequency. The components in the oil are identified by detecting this portion of the light. While the Raman method is pollution-free, it can only analyze macromolecular information in oil. Due to the small amount of information (about 1%) and the high-precision requirements of the equipment, a single unit is expensive, and operation and maintenance costs are high.

The present disclosure describes methods, systems, and devices for simultaneously obtaining the detection results of metal components, particle size, viscosity, and chemical components by means of the spectral characteristics of an oil sample, oil sample sampling point information, and machine learning in a single operation. The disclosed invention achieves the effect of simplifying operation, economizing on consumables, and real-time portable detection. Further, it allows one to take the laboratory into the field and eliminates the need for operation by specialized personnel.

In the process of spectral analysis, multiple spectral bands having the main characteristics within a spectral band range are usually selected for model calculation to detect the target element components and contents. Hyperspectral oil analysis comprises a set of optical systems and algorithmic models. The accuracy and reliability of the optical system and the acquisition of algorithmic models based on the spectral bands of main characteristics—such as elements, ion groups, particle size, and viscosity—permit algorithmic rapid linear regression (convergence), and the resolving of multiple correlations and consistency to determine the quantitative capability of hyperspectral oil analysis.

Since characteristic spectral bands of no two distinct elements completely overlap in nature, the element spectral bands can be extracted to identify and quantitatively analyze elements being detected. When more than one element being detected is present in an oil sample, a series of spectral lines with various wavelengths corresponding to individual elements will appear in the spectral plot, generally within a range of several tens of spectral bands. These spectral bands will be intermixed with the spectral bands of other elements and may even overlap. These spectral bands must be separated, and the target element spectral bands must be extracted to identify and quantitatively analyze the elements.

Until the invention of the present application, these and other problems in the prior art went either unnoticed or unsolved by those skilled in the art. The present invention provides a system and methods using remote hyperspectral sensing technology to produce a relatively lightweight testing instrument. As a result, the disclosed invention achieves notable improvements in testing with the associated device without sacrificing portability, ease of use, and accuracy of results.

SUMMARY OF INVENTION

There is disclosed herein an improved system and scanner for analyzing lubricating oil samples which avoids the disadvantages of prior devices while affording additional structural and operating advantages.

Generally speaking, the system for analyzing fluid for contaminants comprises a fluid sample container for retaining a lubricating fluid sample, a hyperspectral scanner, a hyperspectral library comprised of data relating laboratory reflectance numbers for to an element content in a subject oil, and a server wirelessly connected to the scanner and having processing software to match sample reflectance numbers for each incremental band to laboratory reflectance numbers from the hyperspectral library. System characteristics include ease of operation, quick results, and improving precision as a result of self-learning.

The hyperspectral scanner comprises a light emitter for directing light into the lubricating fluid sample, wherein the directed light has wavelengths in the 400-1000 nm range, a light receiver to receive reflected light from the lubricating fluid sample, and a photoelectric converter for converting incremental bands of the reflected light into sample reflectance numbers.

Further, disclosed is a method for quantitatively analyzing a lubricating fluid for contaminants. Generally speaking, the method comprises taking a sample of a lubricating fluid to be analyzed, directing a light into the lubricating fluid sample, wherein the directed light has wavelengths in the 400-1000 nm range, receiving reflected light from the lubricating fluid sample, converting incremental bands of the reflected light into sample reflectance numbers, providing a hyperspectral library comprised of data relating laboratory reflectance numbers to an element content in a subject oil, matching each sample reflectance number for each incremental band with a laboratory reflectance number from a hyperspectral library, and reporting the element content for each matched sample reflectance number.

Finally, a method for building a hyperspectral library for lubricating fluid analysis is also disclosed. The method comprises collecting a plurality of lubricating fluid samples representing different run-times on a specific machine, analyzing each of the plurality of lubricating fluid samples for quantified element content, scanning each of the plurality of lubricating fluid samples with a hyperspectral scanner to produce a hyperspectral image, measuring reflectance of each of the plurality of lubricating fluid samples at a plurality of intervals within the range of 400 to 1000 nm, plotting the measured reflectance as a data point for each of the plurality of intervals to produce a curve, associating the quantified element content of each of the plurality of lubricating fluid samples with the corresponding curve, and storing each of the curves with the associated quantified element content in a database.

These and other aspects of the invention may be understood more readily from the following description and the appended drawings.

BRIEF DESCRIPTION OF THE DRAWINGS

For the purpose of facilitating an understanding of the subject matter sought to be protected, there are illustrated in the accompanying drawings, embodiments thereof, from an inspection of which, when considered in connection with the following description, the subject matter sought to be protected, its construction and operation, and many of its advantages should be readily understood and appreciated.

DETAILED DESCRIPTION OF A PREFERRED EMBODIMENT OF INVENTION

Figure 1A:
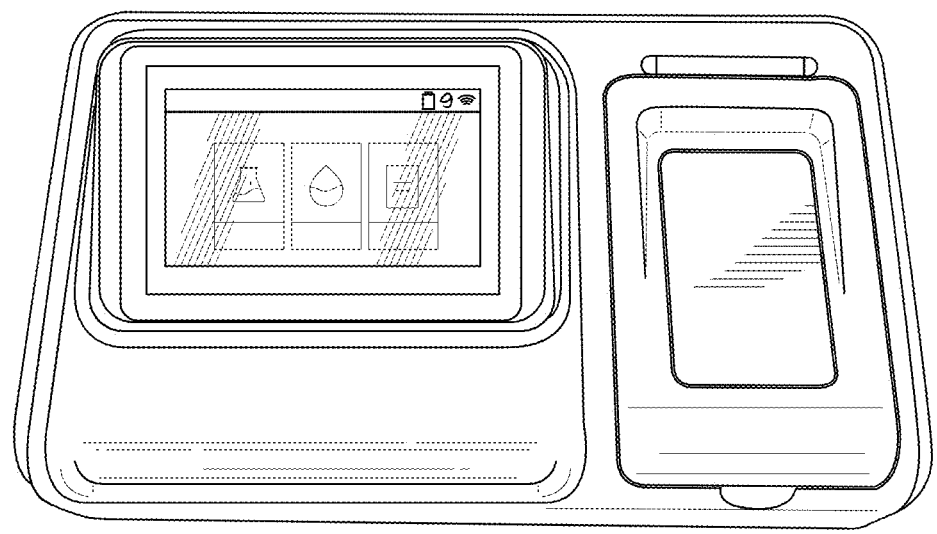
FIG. 1A is a top view of an embodiment of the disclosed hyperspectral lubricant oil analysis device.
Figure 1B:
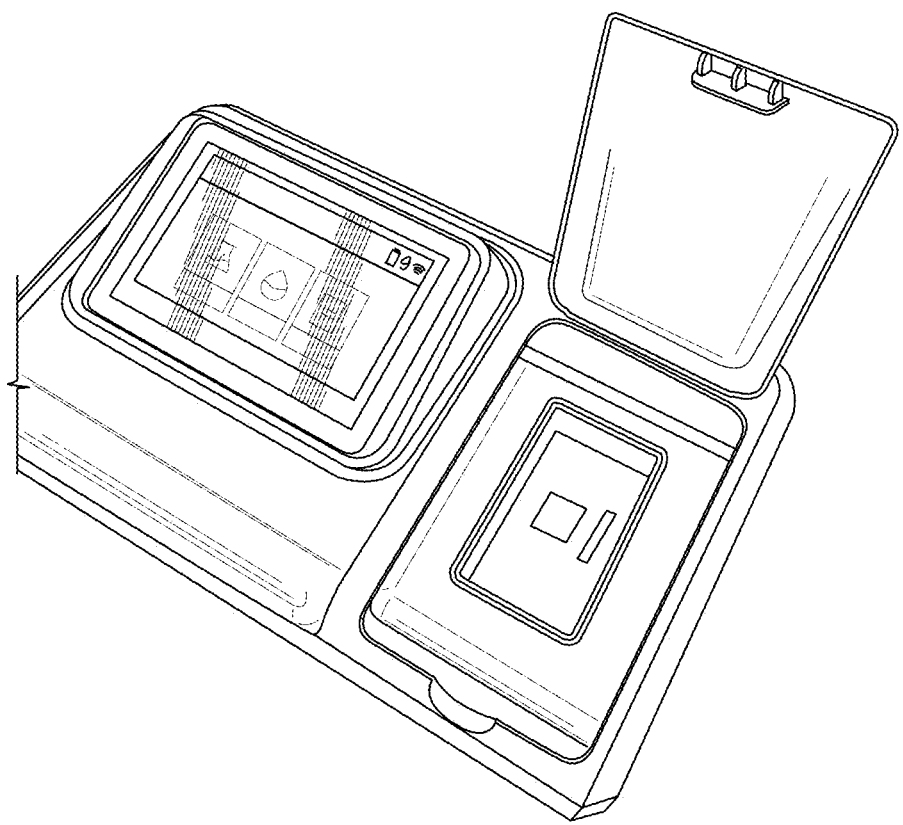
FIG. 1B is a perspective view of the embodiment of FIG. 1A showing the cover open to reveal the cuvette dark chamber.
Figure 2:
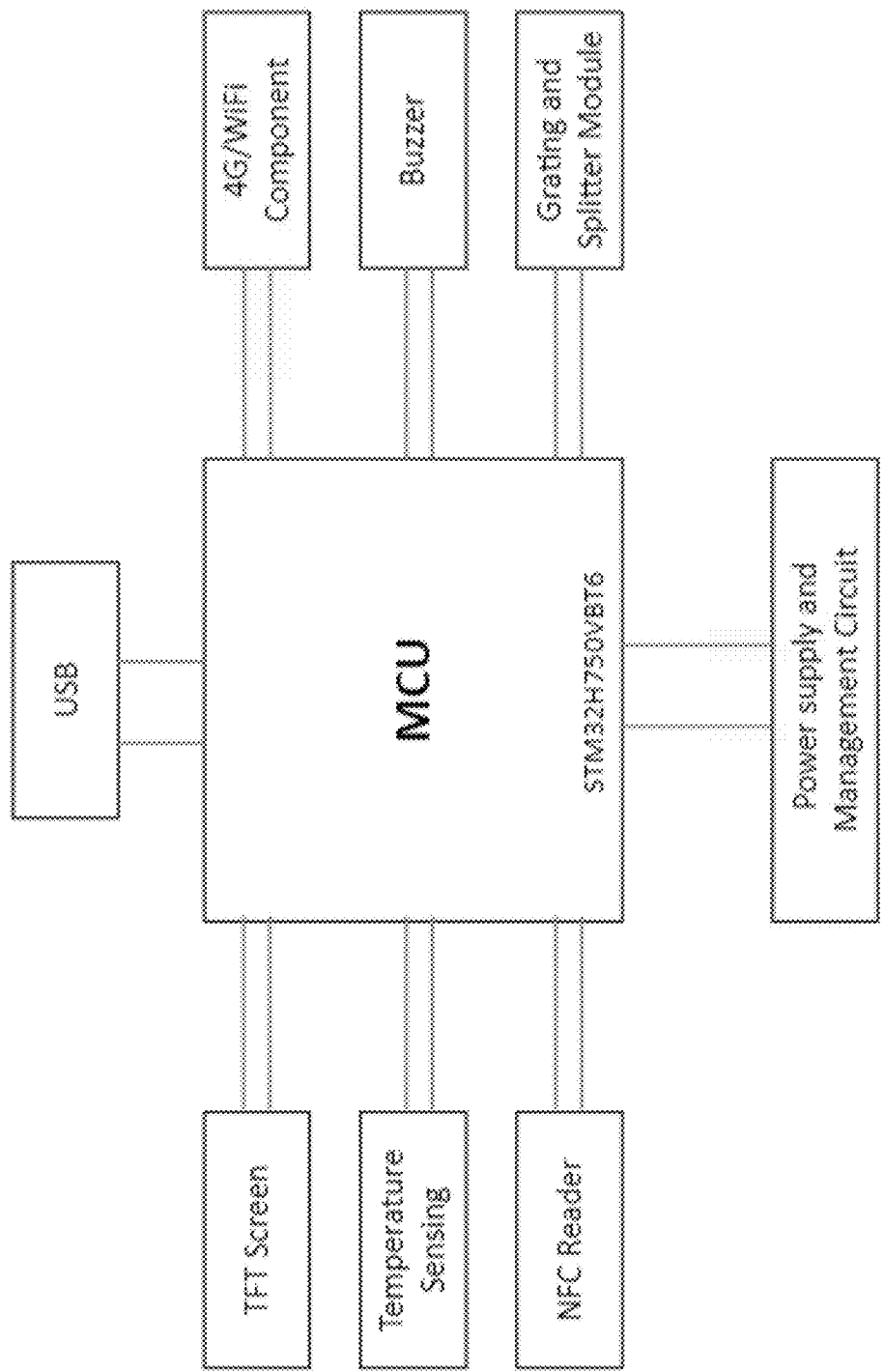
FIG. 2 is a schematic of the device illustrated in FIGS. 1A and 1B.

While this invention is susceptible of embodiments in many different forms, there is shown in the drawings and will herein be described in detail at least one preferred embodiment of the invention with the understanding that the present disclosure is to be considered as an exemplification of the principles of the invention and is not intended to limit the broad aspect of the invention to any of the specific embodiments illustrated.

With reference being made to FIGS. 1-7, a hyperspectral oil analysis system is illustrated and labeled with numeral 10. The preferred embodiment of system 10 is comprised of the analyzer 12, a cuvette 14, and a database 16. Generally speaking, the hyperspectral oil analyzer 12 consists of three core parts: 1) a light source, which is a halogen light projected into the oil sample located in the cuvette container in the dark chamber, and the ion groups (molecular particles) in the oil sample reflect the characteristic spectrum; 2) an optical system, used to collect, distinguish, and identify characteristic spectral bands corresponding to specific ion clusters in the reflectance spectrum, and the characteristic spectral bands are divided by a spectrometer into bands with an accuracy of 2 nm; and 3) a spectral model (not shown) built in consideration of the application scenario, and the data processing algorithm. With the known relationship between spectral bands and corresponding detected elements, a spectral model is established according to the service cycle of the analyzed oil in its liquid or grease form; the characteristic spectral bands of the oil sample are analyzed and processed by the algorithm to calculate quantitatively the results of detection and to show and provide a diagnostic result according to the actual application scenario (i.e., the expert system).

Figure 8:
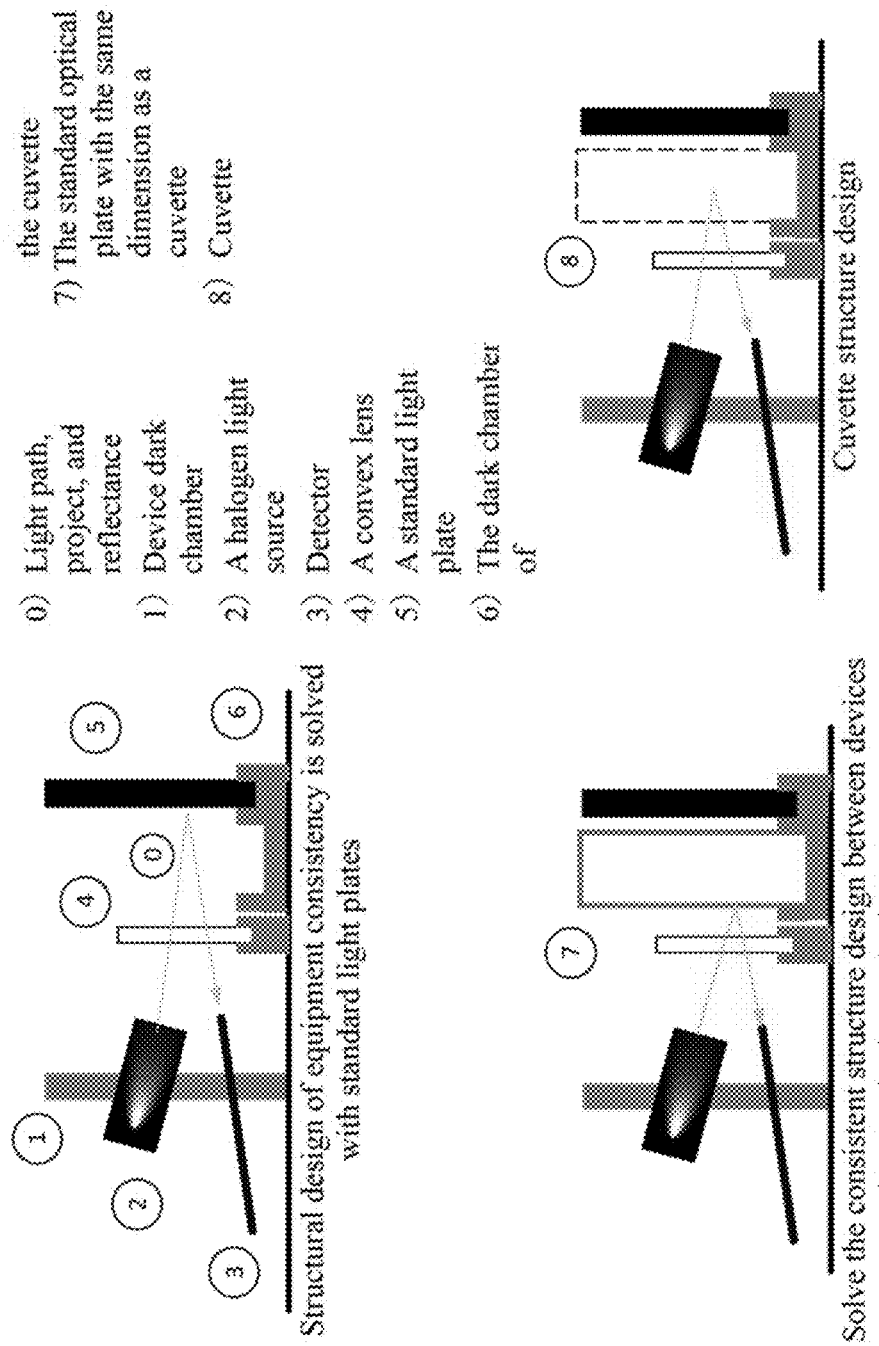
FIG. 8 is a series of schematics illustrating operation of an embodiment of the disclosed analysis device.

As shown in FIG. 8, hyperspectral oil analysis technology uses a reflected light path to obtain the reflectance spectrum of the ion group in the detected oil sample by means of the fixed angle projection of the halogen light. The technology is also used to extract atomic spectral bands (a group of them) with a mathematical method, which simplifies the structural design and the use of consumables. The requirement of the spectral band range is lowered by modeling a range of analyzed oil and inferring measurement algorithms in order to avoid dependence on the ultra-ultraviolet spectral range, which leads to a major reduction of the complexity of the spectral system. In this way, the device can be made portable and more affordable, with real time, simple and smart operation.

A 400 nm-1000 nm halogen light source is used for analysis. The oil sample to be analyzed is loaded into a rectangle cuvette 14 with a volume of preferably about 3.5 ml, having light transmittance on both sides of about +90% (wavelength of 350 nm-2000 nm). The cuvette 14 is inserted into a dark chamber to obtain the spectrum of a specific wavelength (also known as "hyperspectral characteristic bands") through the reflected light path. The reflected light is generally expressed with the characteristic spectral bands of ion clusters (molecules). It is characterized in that its full width at half maximum (FWHM) is wide, and the element (atomic) spectral band (which is very narrow and looks like a line) intrudes into the spectral band. Because there is no complete overlapping of the characteristic spectral bands of two different elements in the world, the spectral bands of the elements are extracted to achieve the identification and quantitative analysis of the detected elements. When more than one detected element is present in the oil sample to be detected, a series of spectral bands of various wavelengths corresponding to each element appear in the spectrum, usually in a range of dozens of spectral bands. These spectral bands are mixed or even overlap with those of the other elements. These spectral bands must be separated to extract the spectral bands of the target element in order to achieve identification and quantitative analysis of the element. In the process of the spectral analysis, multiple spectral bands with main characteristics within the range of the spectral bands are usually selected for model calculation to achieve detection of the components of the target elements and their content. Even so, the hyperspectral oil analysis system consists of a set of optical systems and algorithm models. The accuracy and reliability of the optical system and the acquisition of the algorithm models according to the main characteristic spectral bands of the elements result in a fast linear regression (convergence) for the algorithm, and the solutions of the multiple correlations and consistencies determine the ability of quantitative detection of the hyperspectral oil analysis method.

Based on the output of sampling and the optical system, reflectance and DN values (radiance values) of the oil sample being tested are obtained. Assuming the relationship between the emission spectrum of the element being detected and the intensity of each spectral band corresponding to an element concentration is known, a numeric label for the concentration level (ppm) of the detected element in the oil sample being tested can be calculated. If a sufficient number of oil sample component densities (component densities of all detected elements) and their corresponding spectra with different metal element concentrations have been stored in a database—for example, a model of a number of oil samples for 100 hours and 200 hours of machinery operation—the oil samples being tested between these can be calculated by the principle of partial least squares by adopting the spectral band n as an independent variable $\{x_1, \ldots, x_p\}$ to calculate the test index p as a related dependent variable $\{y_1, \ldots, y_n\}$.

Based on the statistical relationship between a dependent variable and an independent variable, the parameters of the oil sample being tested (the model of the oil sample) among multiple known oil sample points in the system database are observed, and data tables of the independent variable and the dependent variable, $X=\{x_1, \ldots, x_p\}$ and $Y=\{y_1, \ldots, y_n\}$, are formed. Partial least squares regression separately extracts the first components $t_1$ and $u_1$ in X and Y based on the indexes of the oil samples being tested and the corresponding spectral bands based on the capacity afforded by independent variable components to analyze dependent variable components (where the test indexes correspond to known spectral bands). Partial least squares regression implements the regression of X on $t_1$ and the regression of Y on $u_1$, respectively. If the regression equation achieves a satisfactory result (maximization of accuracy or change trend), the algorithm terminates. If a satisfactory result is not achieved, a second round of component extraction is performed using the remaining information after X has been interpreted by $t_1$ and the remaining information after Y has been interpreted by $u_1$. The process is repeated until satisfactory accuracy is achieved.

For example, using a spectrum (reflectance and DN values) obtained from an oil sample being tested after running for 160 hours, if m component $t_1, t_2, \ldots, t_m$ bands are ultimately extracted from spectrum X, a partial least squares regression will be conducted by regressing $y_k$ (the index of some element component) for the $t_1, t_2, \ldots, t_m$ bands in an inversion calculation to obtain a certain element index of the oil sample being tested.

The data processing and quantitative calculation algorithm inputs the spectrum (the split reflectance and DN value) of the oil sample being tested based on spectral model parameters, and quantitatively calculates a detection result by partial least squares regression inversion. In practice, combined with the detection objectives of application scenarios, the actual collection of oil samples and the corresponding laboratory test results are used for one-time calibration of the model.

In the present invention, different models are combined to separate, calculate, and analyze the reflectance and DN values of the characteristics of the spectral bands of oil samples that have been detected once, to separately obtain corresponding detection results for different models. Examples of this are the metal components, particle size, viscosity, and other chemical components. This reduces the detection operation and increases testing speed.

As will be described in detail below, the spectral models are constructed from a set of oil samples that reflect actual application scenario oil changes and correspond to their spectral characteristics. The oil samples cover the entire life cycle of an oil in, for example, manufacturing equipment, such as the entire cycle of lubricating oil in rotating equipment from the replacement of the oil to a subsequent oil change. Based on the specific application scenario, 20 to 30 oil samples are generally selected for modeling.

In practical application, testing accuracy is achieved by obtaining high-quality oil samples or by diluting and mixed modeling of standard oil and actual oil samples. The present disclosure focuses on describing how to apply the algorithm models established based on different test index categories to adapt machine learning to base oil samples. By means of a single detection operation, the detection effect of cross-index types can be achieved.

The proper operation of heavy equipment is critical to a manufacturer. The health of the equipment is evaluated, managed, and maintained through active operation and maintenance to achieve normal operation. The analysis of oil in mechanical equipment is a key link and technique for evaluating the health of equipment. Oil testing complements vibration analysis, thermal imaging, and other predictive maintenance techniques to monitor, diagnose, and assess the health of equipment. However, oil testing is a complex physical and chemical process that mostly still depends on on-site collection for laboratory testing. Unfortunately, mechanical conditions can change significantly within the time required for a laboratory to return oil sample results, such as for aircraft engines. Under certain circumstances, the detected indexes relate to metal components, particle size, viscosity, and chemical components. Examples are lubricating oils and hydraulic oils. Hyperspectral oil testing technical equipment affords on-site oil analysis and real-time detection intended to eliminate long waiting times and achieves comprehensive detection to allow timely decision-making for machine operations.

Figure 19:
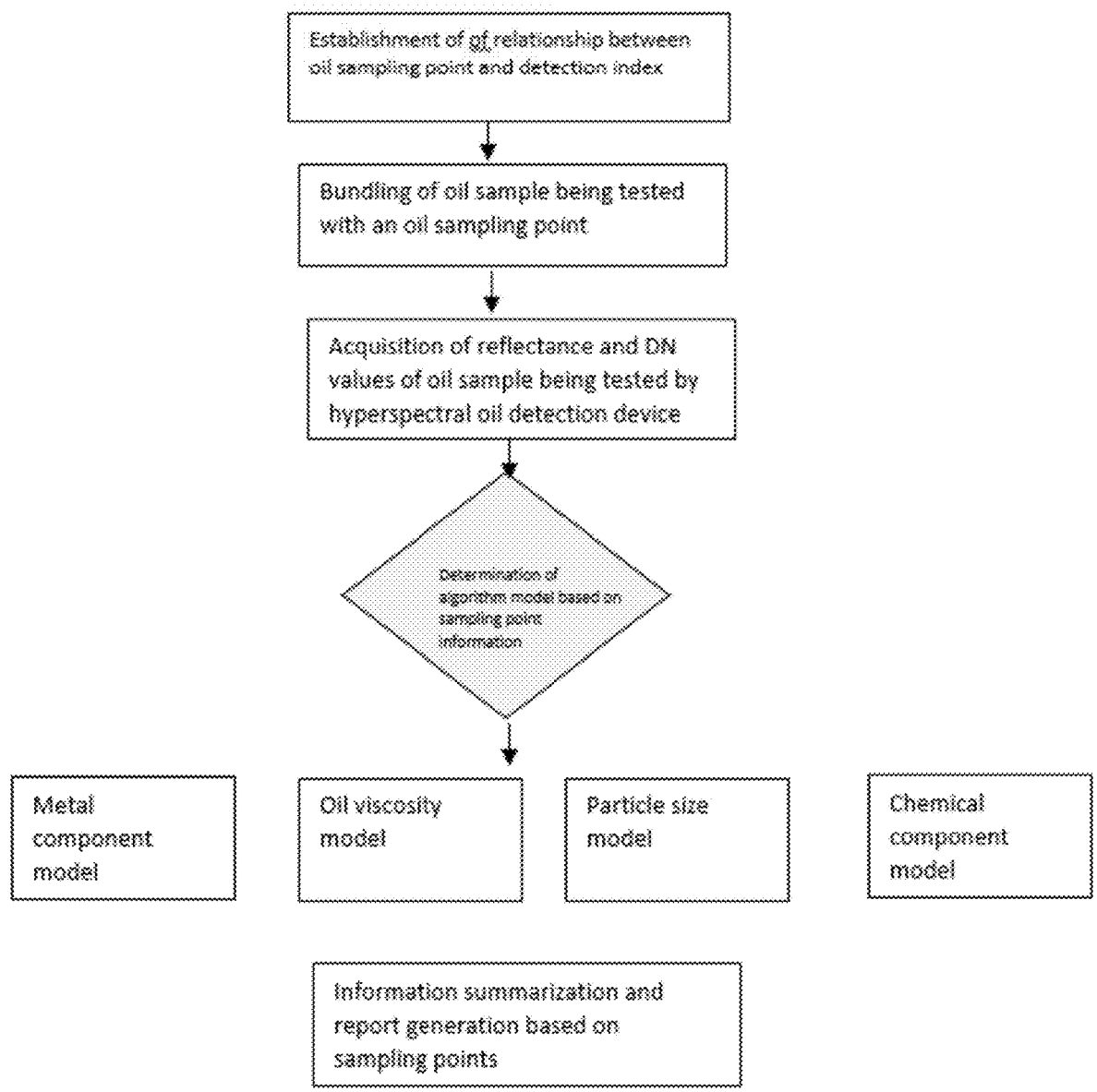
FIG. 19 is a comprehensive detection flow chart of hyperspectral oil detection technique and equipment.

As previously noted, the principle of the hyperspectral oil analysis technique is based on reflectance and DN values obtained from oil samples tested by photoelectric sensors. Model algorithms are used to infer the composition of the oil being tested. Models are established based on the components of oil samples tested using the results of known oil laboratory test components. The same (400 nm-1,000 nm) spectrum, reflectance and DN values from identical oil samples being tested are subjected to different models and corresponding algorithms to obtain corresponding detection results. The results indicate that for a single detection operation, the above mechanisms can be integrated to complete different tests by the following operation process (see FIG. 19):

1) Establishing relationships between sampling points and test indexes. The sampling points are fixed relative to the equipment and the oil it uses. Only the sampling time changes. The component content of the oil samples collected varies depending on the time of collection. The test index refers to the algorithm model corresponding to the hyperspectral oil testing equipment. The algorithm model varies depending on the operating equipment (sampling point), oil brand, grade, and type of test index (such as metal components, particle size, viscosity, and chemical components). The test index and type are fixed relative to the sampling point. By means of hyperspectral oil testing equipment system software (application software), a corresponding relationship is established between the operating device, the sampling point, the oil being tested, and the tested indexes.

2) The oil sample being tested is bundled with the sampling point. The sampling point and the oil sample collection container (for example, a cuvette) are bundled during the collection operation. The sampling point is fixed, and the oil sample container is random. It therefore suffices to establish a relationship between the number, name, or a unique identification (UID) number of the collection container and the sampling point during collection. The sampling point is fixed relative to the equipment and the oil being tested and can naturally be bundled with the oil algorithm model. This operation is based on establishing a relationship between the sampling point and the oil sample model to be tested through the application software during initialization. It is not hard to understand that a sampling point can correspond to multiple model algorithms, and this means that the sampling point must be tested for different types of components. For example, metal components and chemical components may be simultaneously required. The application software runs on a cloud server or on an offline computer. It performs differentiated management, device management (of hyperspectral oil testing equipment), data management (report generation, trend changes, tracing) and the like for the brands, manufacturers, and types of oil samples being tested.

3) The oil being tested is transferred from the collection container to a cuvette, and an oil sample UID number is assigned. The cuvette containing the oil sample is placed in the cuvette dark chamber of a hyperspectral oil testing device. The sampling point is selected through a human-computer interactive page, the number of the oil sample to be collected (optional) is selected/input, and the test operation is executed. The optical system of the hyperspectral oil testing device generates the reflectance and DN values of the oil sample. The reflectance and DN values are bundled with the sampling point and oil sample identification number (or test time if decided not to input identification number) and uploaded to the algorithm model server. After a few seconds, the required test results for that sampling point are returned and displayed. The test results can be retrieved, traced and sorted by number (or test time). The oil sample number is bundled with the sampling point and collection time. Based on the time, the detection results of all of the collected data of the sampling point can be sorted and displayed based on a time axis. The trends of the changes of the oil at the sampling point are clear at a glance. The following describes in detail how the system pushes oil samples to different model algorithms based on sampling points.

4) The model algorithms vary depending on oil performance, brand, grade, operating equipment, and the components being detected. Depending on the application scenario, the sampling point may sometimes be quite sensitive and require a special algorithm to "correct" the existing model or to train the model by machine learning to adapt to the base oil sample (performance, viscosity, contamination, brand, grade). This method will be discussed in detail in the next section. It can be understood here that the model is a parameter matrix A, $$A = \begin{bmatrix} \alpha_{11} & \cdots & \alpha_{n1} \\ \vdots & \ddots & \vdots \\ \alpha_{1m} & \cdots & \alpha_{nm} \end{bmatrix}$$

Herein, n denotes a 400 nm to 1,000 nm spectral reflection band, with 300 discrete spectral lines, and m denotes the number of components of the oil sample being tested, such as 24 metal components. For an algorithm model Y=A⊙X, Y is a mixed reflection spectrum vector, X is a test index vector, A is a model matrix, and ⊙ is an algorithm. Models and algorithms vary depending on the different test components they calculate, while a mixed reflectance spectral vector does not vary. Test index (category) vectors, calculation results, and algorithms and model matrices differ and are distinguished. A hyperspectral oil testing equipment system will establish an algorithm model library based on oil performance, brand, grade, operating equipment, detection components, and sampling points. The application software "connects" (bundles) different model algorithms based on sampling points. When a detection operation selects a sampling point, the application software determines which model algorithms need to be called for the reflectance and DN values obtained by the collection operation based on the settings.

5) The application software spawns threads based on different model algorithms, and simultaneously pushes the reflectance and DN values of the oil sample being tested to each thread for model calculation. Since the algorithms of each model are independent, the amount of data for unified input of the reflectance and DN values of the oil samples being detected are limited, thereby resulting in independent vertical technology permitting parallel operation. Therefore, the calculation time will not increase due to an increase in the test types at a certain sampling point. For the user, the detection operation of the hyperspectral oil testing equipment is unrelated to the number (types) of detection categories. The user clicks on the execution button on the human-computer interactive page of the device, and the detection results can be displayed within 5-6 seconds.

The application software focuses on cross-model detection (multi-models). When calling the model (detection) for the first time, the model must be based on a sample of the base oil. Adaptive learning improves detection accuracy. The first call (based on a sampling point) can be assigned to device initialization. The adaptive learning logic is discussed in detail in the next section.

6) In the detection data summary, the result report generates an operation process containing distribution calculations and a synchronized result data summary. Computation synchronization monitors the running of all threads to ensure that the operation of the last algorithm model thread has been completed and results have been generated. Then the results of all thread operations are summarized, and the results are pushed to the front end application based on the data and the report format. When a certain thread is still being calculated, all results are summarized and pushed to a front end application. The results of threads whose operations have not yet been completed become indeterminate data or erroneous results. The delay caused by synchronizing the operation results of each thread should be on the order of microseconds or milliseconds, which will not affect the displaying of results or the operational experience of the end customer.

When multiple threads run independently at the same time and the start and completion times differ, synchronization (a software-specific function) must be used to ensure that all threads are completed before fetching the results (or continuing to the next stage of operation). Otherwise, the results will be incomplete (software-defined results at this point may not be useful). Here, ensuring that the last algorithm model thread operation has ended (which is random) refers to the software function of synchronously monitoring completion of the threads.

In general, specific oil samples are used for equipment modeling. The model that is established is extremely sensitive to the base oil manufacturer, brand, grade, viscosity, and degree of (particle) contamination. Cross-model testing of identically collected oil samples, such as the detection of metal components, chemical components, and oil viscosity, cannot guarantee that the base information of the oil sample being tested (such as No. 0 oil) will match the modeled oil sample, and this inevitably interferes with the model and affects accuracy. The model must be re-learned based on the sampling point (oil sample) to achieve relative detection accuracy. The method of adaptive relearning is a key link in the implementation of automated cross-model detection. The method adopted is folded (subset) interleaving to predict responses. In this "prediction," the partial least squares modeling prediction (detection) described in the technical principles of this invention is adopted. Some of the subsets are used for observation, the number of subsets is related to the distribution gradient of the oil sample group being modeled, and the result "response" is measured by the mean square error (MSE).

$$MSE=(1/k)*\Sigma(y_i-f(x_i))^2$$

Here, k denotes the number of the model prediction learning cycle, which is determined by the distribution gradient of the oil sample group; $y_1$ denotes the $i^{th}$ observation response; and $f(x_i)$ denotes the $i^{th}$ prediction learning result (detection value). The better the model learns to predict the observed value, the smaller the MSE.

The detection model requires the establishment of the distribution of multiple oil sample points through the entire life cycle of the oil. The oil sample batches provided by customers are often in a certain area (point) in the oil sample life cycle distribution. Diluted (oil sample) modeling accordingly becomes necessary. A "representative" oil sample is selected in the batch of oil samples to be diluted with the base oil (no. 0 oil) to establish a distribution gradient and constitute an oil sample group for modeling. The subset refers to the sum of the prediction and training sets in the folded subset interleaved prediction response method, which depends on the distribution gradient and must be smaller than the number in the sample group of the oil being modeled.

The reason why this depends on the distribution gradient (correlation) is that each dilution point (point of the distribution gradient) can be understood as a model parameter matrix point. A continuous area is formed between the matrix points by fitting (by the partial least squares method). Therefore, a known oil sample (with test results) and a base oil are used for dilution to form distribution gradient points (training and prediction sets). The results for each point are known. It is used in this manner to train and improve existing models. The accuracy of the distribution gradient points (known) depends on the specific gravity volume dilution method.

Figure 16:
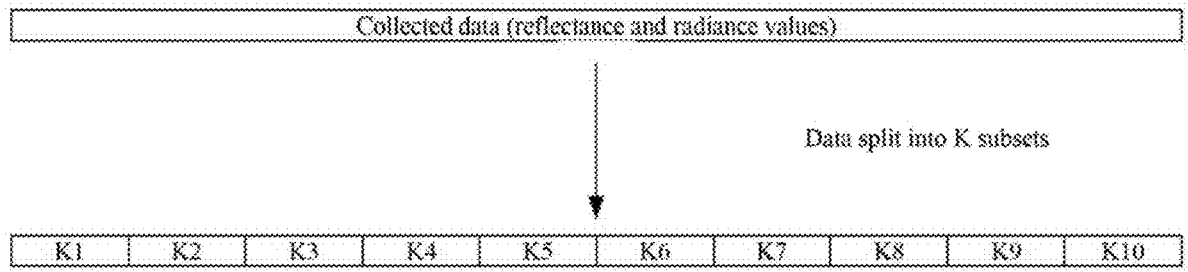
FIG. 16 is a schematic diagram showing the splitting of data into several subsets.
Figure 17:
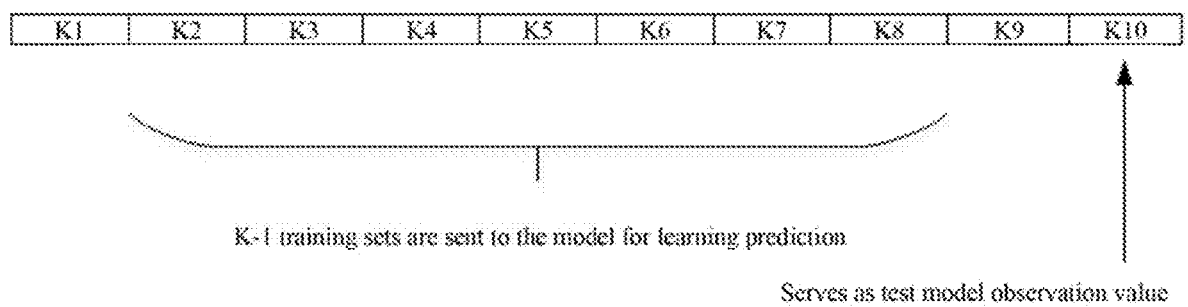
FIG. 17 is a schematic diagram showing the division of the collected data into a training set and a prediction set.

The present invention uses the following principles to calculate the MSE for a given model:

1. Dividing the collected data into a training set and a test set based on the modeled dilution gradient distribution or a dependent variable (key test index element), as shown in FIG. 16.
2. Refining the model using only the data in the training set (machine learning). Using the model to make predictions (observations) on the test set and calculating a response test MSE. This is shown in FIG. 17.

Repeating the above steps k times, each time using a different training and test set (different gradients for modeling oil samples). Depending on the number of iterations the model is trained on, the predicted value will approach ever closer to the output of the model training set.

Figure 18:
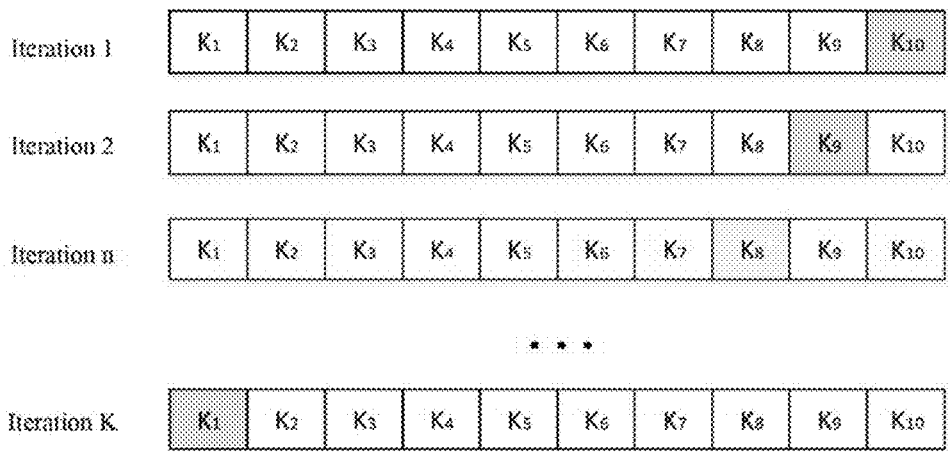
FIG. 18 is a schematic diagram of the repeated iterative improvement of a prediction model and observation feedback.

The overall test MSE is calculated as the average of k test MSEs, shown in FIG. 18.

In practice, the following procedure is used to calculate the MSE for a given model:

Actual sampling point oil samples with laboratory test results are diluted by the volume specific gravity method and combined with the base oil (no. 0 oil) based on a concentration gradient to obtain a group of oil samples of known distribution. The oil sample group is generated by a hyperspectral oil analysis device to generate a set of reflectance and DN values. Among these, based on the spectrum, each group of DN values corresponds to a reflectance group, $$R(K_i) = \sum_{i=0}^{K} \left( \frac{R(K_i)_{DN} - \text{dark current}}{R(\lambda)_{DN} - \text{dark current}} \right)$$

$R(\lambda)_{DN}$ is the standard plate DN value (obtained when the equipment is turned on and calibrated every day), $R(K_i)_{DN}$ is the DN value of the oil sample being tested at the distribution gradient $K_i$ position, and $R(K_i)$ is the reflectance at the distribution gradient $K_i$ position of the oil sample being tested. The dark current is the DN value (also known as the background noise of the equipment in the dark chamber, which is obtained when the equipment is turned on and calibrated every day) obtained by the hyperspectral oil testing equipment without any light source illumination. $K_i$ is the test set, and the series of reflectance and DN values other than $K_i$ are the training set.

3. The series of reflectance and DN values other than $K_i$ are entered into the model one by one. The model uses the partial least squares method to analyze the statistical relationship between dependent variables and independent variables.

Figure 10:
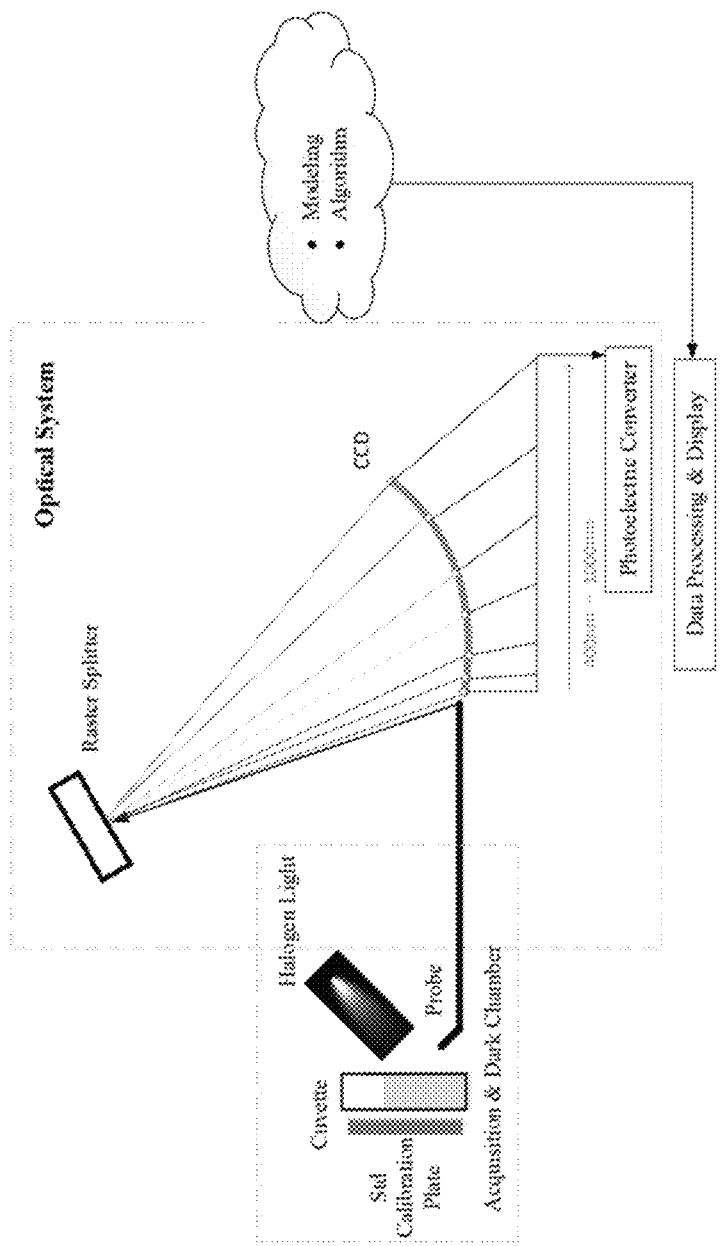
FIG. 10 is a schematic illustration of the principle of the disclosed lubricant analysis device based on reflected hyper-spectrum.

As illustrated in FIG. 10, the acquisition and optical system of the hyperspectral oil device consists of a halogen light source, a dark chamber with a calibration standard light plate provided for the oil sample cuvette, a probe forming an angle with the light source, a grating splitter, and a photoelectric conversion module with a photoelectrically coupled complementary metal oxide semiconductor (CMOS).

The halogen light source and the probe for collecting the reflectance spectrum are located on one side of the dark chamber, and the standard light plate is fixed on the other side of the dark chamber. Without a cuvette inserted, the light source can be projected to the standard light plate, and the reflected light can be directly received by the probe. The setting of the structure provides the operation needed for the calibration of the hyperspectral oil analysis device upon its being turned on once a day.

The cuvette 14 loaded with an oil sample to be tested (<3 ml) is inserted into the dark chamber and a "sealing" lid is closed to prevent pollution by the light from outside the chamber. Then, the light source can be directly projected horizontally (laterally) to the cuvette 14 and pass through the light transmittance surface of the cuvette, which has a transmittance rate of more than 90% (350 nm-2000 nm), then to the oil sample, with a certain level of penetration and reflection. Depending on the incident angle, the reflectance spectrum passes through the light surface of the cuvette 14 and goes directly into the probe.

Figure 11:
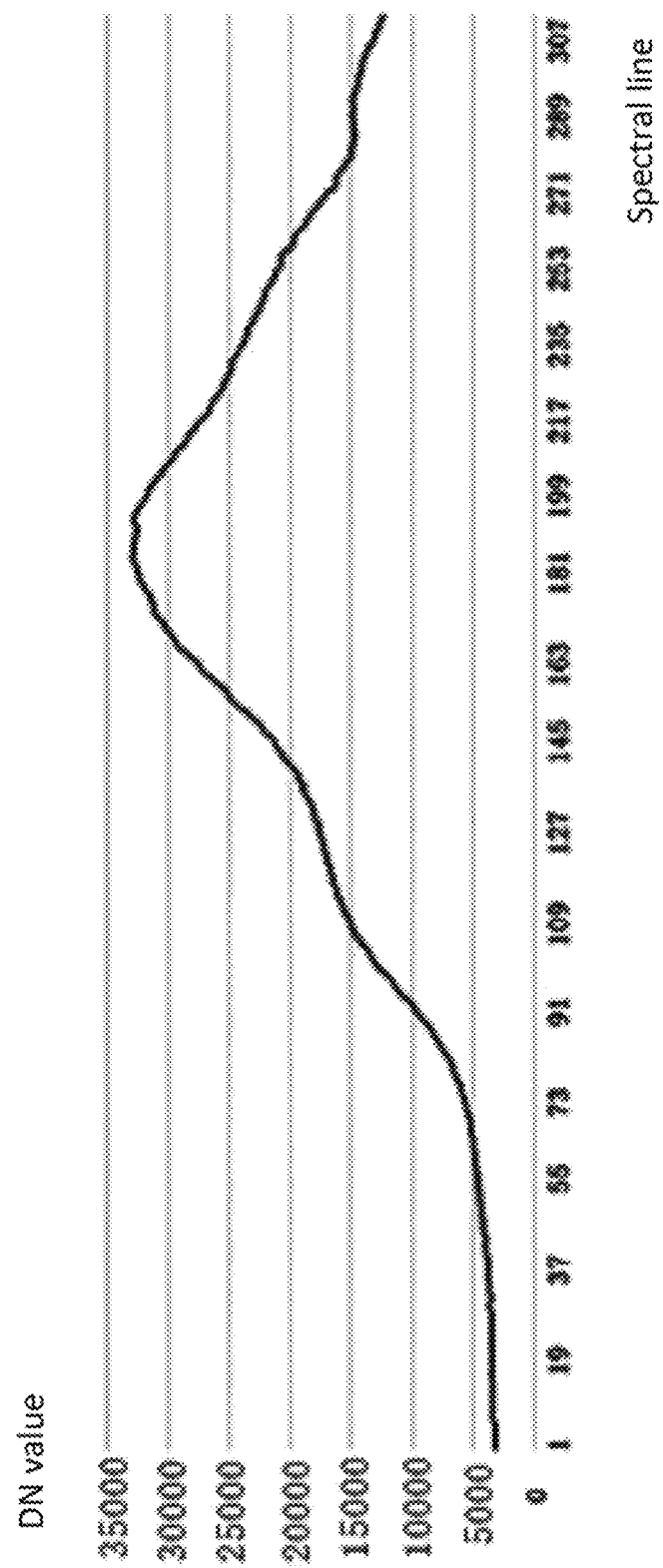
FIG. 11 is a graph showing DN values of spectral (wave) band corresponding to tested oil samples.

The optical system transmits the reflectance spectrum of 400-1000 nm that has entered the probe to the diffraction grating. The grating divides the reflectance spectrum into 300 discrete (non-continuous) characteristic lines with the accuracy of 2 nm of spectrum band, which is similar to the monochromatic light of a single wavelength (1 nm). A photoelectric conversion of characteristic spectral lines is conducted via the electrically coupled complementary metal oxide semiconductor (CMOS), a charge coupled device (CCD), or a photomultiplier tube (PMT) to produce a group of real radiance values LDN with the wavelength ($\lambda$) as a variable, which can lay a foundation for subsequent data processing and quantitative analysis. This group of radiance values is also called DN values (digital number-intensity); see FIG. 11.

The conversion of the remote sensing reflectance rate is subject to interference by many factors, including the intensity of the light source, the integration time, the CMOS saturation efficiency, and the temperature. These factors keep changing even in a fixed environment and vary from device to device. Through the calculation and conversion of the remote sensing reflectance rate, the interference by these factors can be corrected or eliminated to achieve real changes that reflect the components of the oil sample to be analyzed. The reflectance rate of the tested oil sample $f_\lambda$ is calculated as follows:

$$f_\lambda = L_{DN}(\lambda) * R(\lambda) / \pi R(\lambda)_{DN}$$

$L_{DN}(\lambda)$ is the true radiance lightness value (DN) received by the probe in a given band, $R(\lambda)$ is the reflectance rate of the standard plate, and $R(\lambda)_{DN}$ is the measured radiance lightness value of the standard plate (DN). $R(\lambda)$, the reflectance rate of the standard plate, is based on the intensity of the standard white plate, written as White $(\lambda)$, and the intensity (dark current) of the black plate, written as Black $(\lambda)$. $R(\lambda)$ is obtained by calculating the ratio of the reflectance value of the halogen light source and the reflectance value of the standard light plate to the halogen light source.

$$R(\lambda) = \sum_{\lambda=0}^{300} \left( \frac{R(\lambda)_{DN} - \text{Black}(\lambda)}{\text{White}(\lambda) - \text{Black}(\lambda)} \right)$$

Ideally, the value of reflectance of a standard white plate should be close to the total reflectance, and the value of the reflectance of a black plate should be close to zero. The value of reflectance of an oil sample should be between the values of reflectance of a white plate and a black plate. Therefore, the reflectance rate $f_\lambda$ should be in a range of 0 to 1.0. The reflectance rate of the standard plate can be used to calibrate the deviation caused by interference factors.

Figure 12:
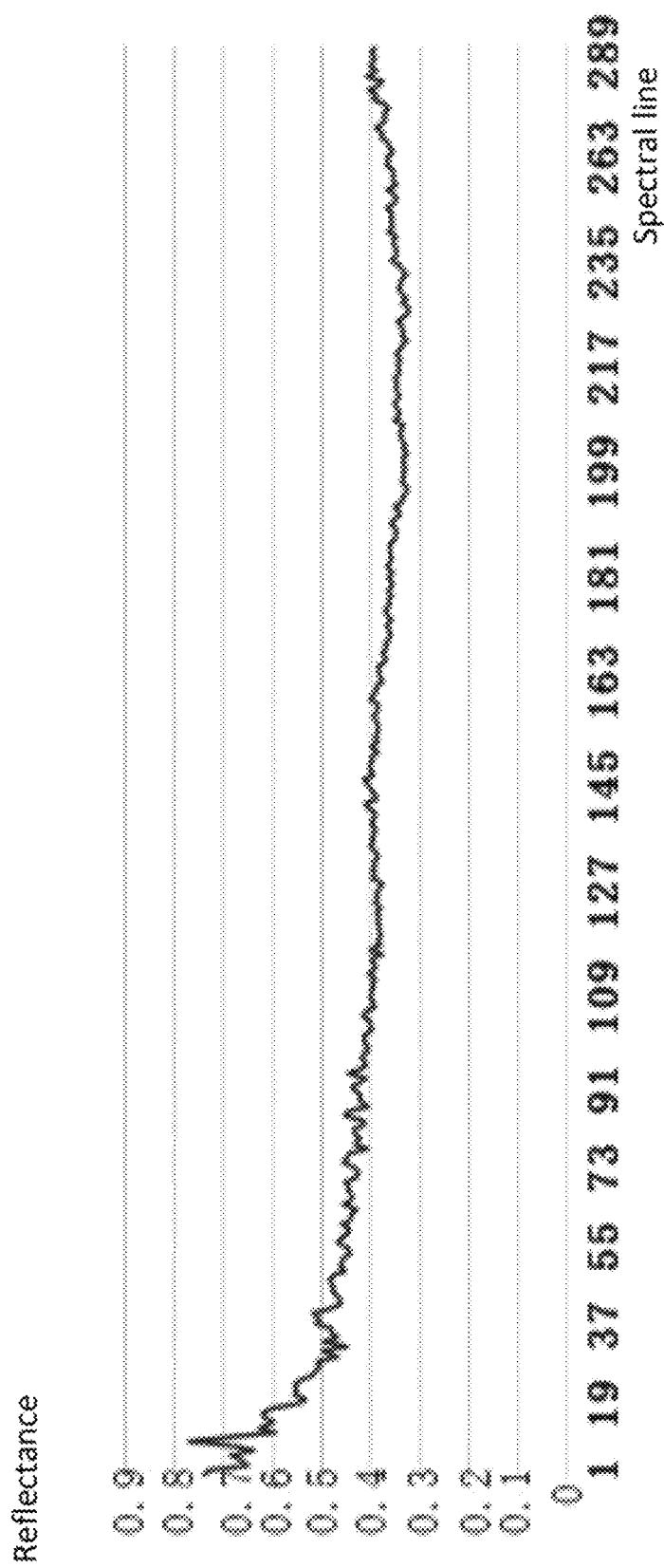
FIG. 12 is a graph showing the reflectivity of spectral (wave) band corresponding to tested oil samples.

FIG. 12 shows the reflectivity $f(\lambda)$ of the oil sample being tested corresponding to the 400 nm to 1,000 nm band. The reflectivity represents the intensity of the spectral lines obtained in this band, also known as the optical density value. The optical density value is directly used to calculate the concentration level (ppm) of each metal in the oil sample being tested.

The reflectance rate represents the intensity of the spectral lines obtained in that band, which is also known as the optical density value. The optical density value is directly used to calculate the concentration grade (PPM) of the content of each metal in the oil sample being analyzed.

The reflectance rate and the DN value of the oil sample are obtained according to the output of the acquisition and optical system. Should the emission spectrum of the detected element and the relationship between the intensity of each spectral band and the concentration of the corresponding element be known, the numerical label of the concentration grade (PPM) of the detected element in the oil sample can be calculated. If in the system database there is a sufficient amount of density (the concentrations of content of all detected elements) distributions of oil samples with varied concentrations of different metal elements and their corresponding spectra—for example, the models of several oil samples in the 100-hour and 200-hour run time interval—the oil samples between them can be calculated by using the principle of the partial least squares regression, with the spectral band n taken as the independent variable $\{x_1, \ldots, x_p\}$ to calculate, with the detection index p as a dependent variable $\{y\ 1, \ldots, y_n\}$. According to the statistical relationship between the dependent variable and the independent variable, the parameters of the tested oil sample (from the model of the oil sample) in the middle of several known oil sample points in the system database are observed, from which the data table of the independent variable and the dependent variable is established: $X=\{x_1, \ldots, x_p\}$ and $Y=\{y\ 1, \ldots, y_n\}$. The method of the partial least squares regression is used in X and Y respectively to extract the first component $t_1$ and $u_1$ according to the indicators of the oil sample to be detected and its corresponding spectral band, based on the analytical ability of the independent variable component $v_s$ the dependent variable component (the detection indicators are corresponding to the known spectral bands). Partial least squares regression implements the regression of X on $t_1$ and the regression of Y on $u_1$, respectively. If the regression equation achieves a satisfactory result (reflected by the maximization of accuracy or trend of change), the first round of components are calculated. The remaining information after X is interpreted by $t_1$ and after Y is interpreted by $u_1$ is used for the extraction of the second round of components. The process is repeated until a satisfactory accuracy of each component is achieved. For example, for the spectrum (the reflectance and the DN value) obtained from the tested oil sample running for 160 hours. If eventually m component $t_1, t_2, \ldots, t_m$ bands are extracted for spectrum X, partial least square regression will be carried out through the implementation of $y_k$ (the indicator of a certain element) to conduct an inversion calculation for the regression of the $t_1, t_2, \ldots, t_m$ bands, to obtain the indicator of a certain element of the oil sample.

In the data processing and quantitative calculation algorithm, according to the spectral model parameters, the spectrum of the oil sample (the reflectance frequency and the DN value after being split) is entered, and the results of detection are quantitatively calculated with the method of partial least square regression inversion. In practice, the actual oil samples of the application scenario and the laboratory test results are combined to conduct a single standard comparison. However, the disclosed invention provides a method for ensuring that the reflectance frequency and the DN value of the oil sample are not affected by the detection device, and a method in which they can be automatically calibrated by data preprocessing.

Device Calibration for Consistency of Operation

As previously described, the accuracy of the hyperspectral oil reflection analysis technology depends on the consistency of the device, the workability of the technical principle, and the accuracy of the calculation method. The latter can be achieved by establishing a model of the standard oil in combination with actual oil samples. Features of this invention focus on describing a method of design and verification of device consistency. The results of repeated testing of the same oil sample by the device system reflect the repeatability of the device. The results of the same oil sample tested on different devices reflect the consistency of the device. The consistency (i.e., both consistency and repeatability) of the device is the basis for the device to reach a high level of accuracy. The factors that affect device consistency include light source stability, stability of grating splitting and photoelectric conversion, the consistency of structural design and the associated operations, and the impact of environment (e.g., temperature, humidity) on the optical path and grating circuit.

The consistency of device components is related to the light source and the grating separation and the photoelectric conversion circuit. The controllable parameters are exposure time (an integral value) and gain. The results are expressed with the reflectance rate and the DN value according to the band. With the length of use and environmental factors, the deviation of the parts of the device can be reflected by the changes of the reflectance rate and the DN value. The structural design and installation of the device can cause inter-device differences, the results of which are also reflected by the changes of the reflectance rate and the DN value. During operation of the device, a slight difference in the position and angle of the insertion and extraction of the cuvette will directly affect the reflectance angle of the optical path, the results of which are also reflected by the changes of the reflectance rate and the DN value. The quality of the light transmission surface of the cuvette falls under the subject of material selection for the cuvette. The cleanliness of the light transmission surface of the cuvette can be controlled by operation procedures, so it is not within the scope of this discussion.

To sum up the problems described above, consistency can be reflected by the changes of the reflectance rate and the DN value. If a relationship can be established between a) changes in the reflectance rate and in the DN value and the prostration of the properties of parts and components with use over an extended period of time, b) changes in the environment, c) variations in the structural design, and d) influence of human operations, so that the changes can effectively be calculated (measured), then device consistency can be ensured by correcting the measurement deviations (with the methods of reverse change or compensation).

With reference to FIGS. 5-7 and 10, consistency deviation of the device can be measured by installing a standard light plate 4, inserting a structural cuvette into the extraction structure, and introducing a standard module light plate that is of the same size as the cuvette (3D). The design method also includes calibration and consistency testing methods.

The halogen light source and the probe grating splitter are fixed by the dark chamber structural component of the device. Thus, a projection light path angle and reflectance angle are also determined. The structural component of the dark chamber of the cuvette establishes a fixed relationship with the light path (i.e., the light source and probe grating splitter) through the center of the light-transmitting lens. A fixed standard light plate is installed on the standard light plate slot of the structural component of the dark chamber of the cuvette, so that the light source is projected onto the standard light plate and the optical path reflected off the grating splitter of the probe is determined. Assuming little to no light pollution (i.e., light is not leaked) in the dark chamber of the cuvette, a special coating on the standard light plate makes it possible that the reflectance rate and intensity (the DN value) are not affected by the ambient temperature and humidity.

After the device is assembled, a measurement should be made and the reflectance rate and the DN value recorded as the "initial state" of the device. Therefore, the reflectance rate and the DN value obtained when the device is tested at any different time periods (e.g., after it is turned on for the first time every day), will be different to those recorded at the initial state. This difference indicates that deviation from consistency exists with the device. Deviations may be caused by environmental factors and/or functional attenuation of the light source and the probe grating splitter after use over time.

The design and processing of the structural parts of a device, the assembly of the halogen light source and the probe grating splitter, as well as the assembly of numerous devices, will certainly result in slight differences between devices. Such difference can be exhibited in reflectance rate and DN value by way of the optical path. Therefore, deviation consistency between devices needs to be measured.

To measure deviation consistency between devices, a standard module light plate is custom made according to the size of the cuvette—i.e., at least one side of the cuvette is equipped with a standard light plate. The standard module light plate is of the same size with the cuvette, and it is inserted into the cuvette hole in order to measure the difference between the operations of extracting and inserting a cuvette on different devices. The method of measurement is to first set a device as the "benchmark" for all other devices.

A standard optical surface of the standard module optical plate facing the optical path (the direction of the see-through lens) is inserted into the cuvette hole, and the reflectance rate and the DN value are tested after the device is turned on and warmed up. Values are then recorded as the "initial state" of the benchmark machine. The reflectance rate and the DN value are stored on a spectral model server (i.e., a dedicated server) and bound to the specific model built with the benchmark machine. For other devices, testing with a standard module optical plate will be conducted after being assembled or periodically (e.g., at times of maintenance or repair), and their reflectance rates and the DN values recorded. Each time a device carries out an oil analysis, the reflectance rate and the DN value data of the device are bound to the reflectance rate and the DN value of the standard module optical plate, and the data is uploaded to the spectral model server. Before recording and storing the measured reflectance rate and the DN value of the oil analysis data, the spectral model will first analyze the reflectance rate and the DN value of the standard module light plate of the uploading detection devices and compare these with the reflectance rate and the DN value of the modeling benchmark machine. From this comparison, measurement error, if any, can be obtained. The spectral model will then correct the reflectance rate and the DN value of the oil analysis data according to the measurement error of each band, so that the test results are consistent with those of the benchmark machine.

The oil sample to be analyzed is first injected into the cuvette 14, and the cuvette 14 is then inserted with its transparent surface facing the light path (i.e., in the direction of the see-through lens) into the dark chamber. The dark chamber is closed to prevent external light from leaking into the dark chamber, and then operation of the device is commenced. Although the entire analysis operation takes only a few seconds (i.e., the testing itself will take about 5 to 6 seconds), inserting and extracting the cuvette containing the oil sample are independent and random events for both the device and the spectral model in the server. Therefore, the results of the continuous/repeated analysis of the same cuvette in the cuvette hole should be consistent (repeatable), as will any results of analysis. From the point of structural design, the implementation of the insertion and extraction actions require a space between the cuvette and the cuvette hole. Strictly speaking, any gap in the cuvette hole will introduce an error (angle) to the light path, resulting in a difference between two independently operated events, even though the same cuvette containing the same oil is being analyzed.

Figure 5:
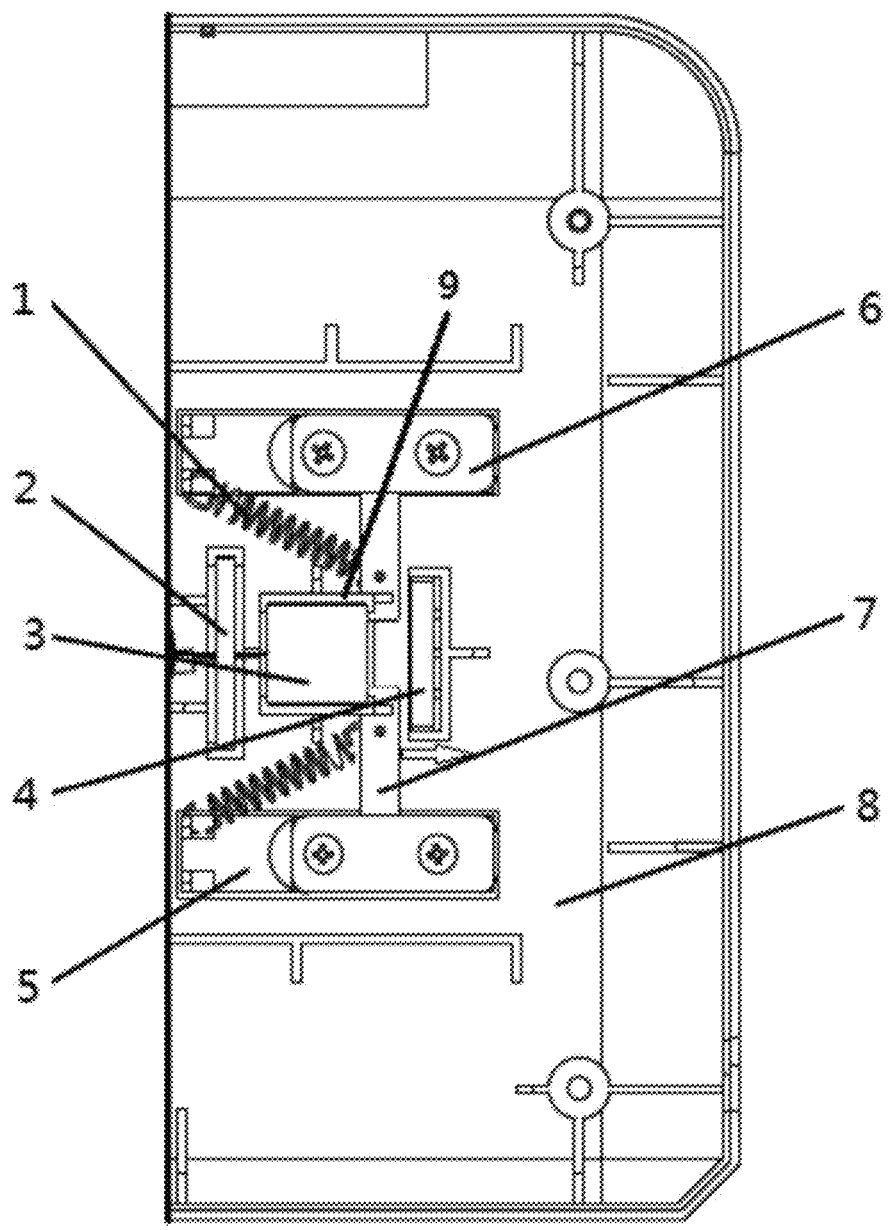
FIG. 5 is a vertical view of the structure of the dark chamber of the cuvette.
Figure 6:
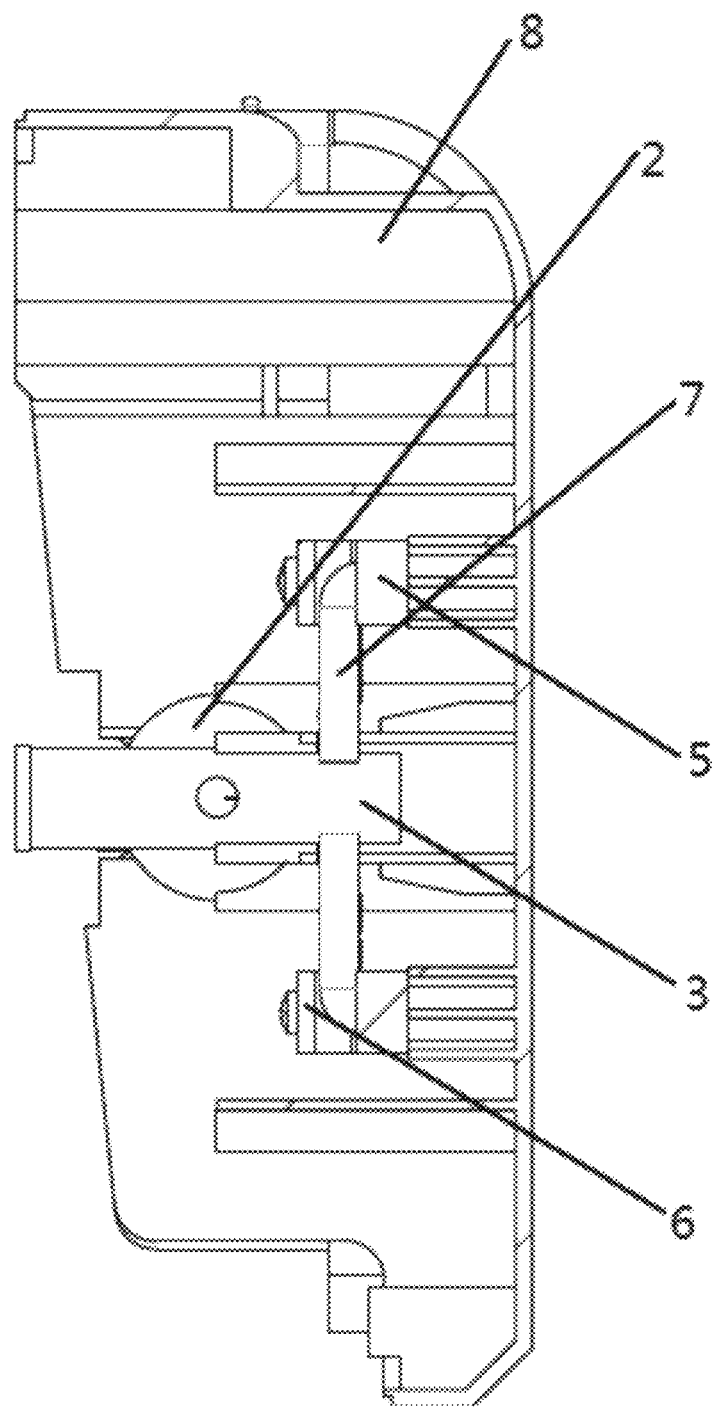
FIG. 6 is a front view of the structure of the dark chamber of the cuvette.
Figure 7:
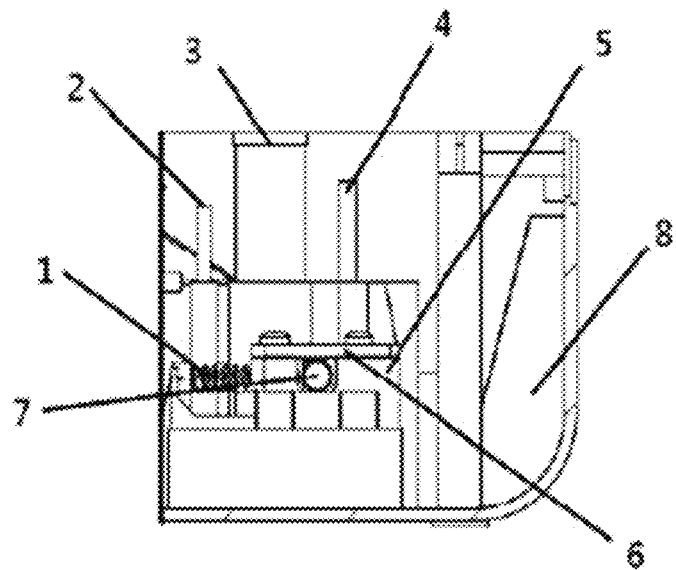
FIG. 7 is a side view of the structure of the dark chamber of the cuvette.

Regarding structural design of the dark chamber, the action of inserting and extracting the cuvette 14 containing the oil sample must be considered. It should not only be easy to operate, but also ensure that the structure of the dark chamber can hold the cuvette seamlessly. For example, the insertion into the transparent surface of the cuvette must not result in a fine angle in the light path. FIGS. 5-7 are schematic diagrams of an embodiment of the dark chamber structure, and a notable key is to fix the rotating shaft (a columnar structure) of the cuvette. The following is a description based on a vertical view of the dark chamber structure shown in FIG. 5.

The structure of a preferred embodiment of the dark chamber consists of a cuvette hole 9, a light-transmitting lens bracket and a see-through lens 2, a cylindrical rod for fixing the cuvette—namely, rotating shaft 7—and the cylindrical rod mechanism of the cylindrical rod for fixing the cuvette—namely, the rotating shaft seat 5, which ensures that the rotating shaft 7 moves in only one direction, as indicated by the arrow in FIG. 5—and the standard optical plate 4.

Installation begins by placing the rotating shaft seat 5 on the lower cover 8, then inserting the rotating shaft 7. Once the rotating shaft seat cover 6 is closed, attachment of bolt and installation of spring 1, to connect the rotating shaft 7 with the rotating shaft seat 5, follows. Finally, the see-through lens 2 and the standard light plate 4 are placed in the convex lens slot and the standard plate slot on the lower cover 8.

When the cuvette 3 is inserted into the slot, pressure exerted by the cuvette 3 pushes the rotating shaft 7 to rotate horizontally. As the cuvette 3 reaches the bottom, and the spring 1 pulls the rotating shaft 7, thereby pressing against the cuvette 3 and fixing the cuvette 3 to prevent it from shaking in the cuvette hole 9.

The cuvette hole 9 is designed according to the size of the cuvette 4, and sufficient space is necessary to ensure the smooth insertion and removal the cuvette. The distance and parallelism between the transparent surface of the cuvette 4 and the light transmitting lens 2 are guaranteed by the two rotating shafts 7 via spring 1 and rotating shaft seat, which are used to fix the cuvette 4. Because the rotating shaft is inserted into the cuvette 4, it is subjected to a force causing it to move in the opposite direction of the transparent surface of the cuvette 4. Such movement causes tension in the spring 1, which in turn causes the cylindrical rod 7 to press on the transparent surface of the cuvette 4 to stabilize it. The assertion of a force does not hinder the operation of inserting and extracting the cuvette 4. An elastic "soft" material is preferably used to make the rotating shaft 7, so that the transparent surface of the cuvette 4 will not be worn out as a result of repeatedly being inserted and extracted.

Consistency Testing and Calibration

Consistency testing is for the testing and verification of the structural design and assembly quality of the dark chamber. As previously noted, one-time testing is preferably carried out and recorded after the device has been manufactured to establish an "initial state" of each device. The consistency calibration method is based on the record of the initial state of a device (i.e., reflectance rate and the DN value). In the course of use, additional reflectance rate and the DN value data are obtained through an efficiency test of the device when it is turned on for the first time every day. This data is then compared with the initial state record for calibration to be carried out and ensure consistency of the device.

Real-time operations can be thought of abstractly as the process of inserting, testing, and extracting the cuvette. The cuvette dark chamber structure needs to verify each insertion, close the cover of the dark chamber, start the test, and maintain the parallel position and distance between the cuvette and the light-transmitting lens. To describe this by another method, the reflectance rate and the DN value projected by the optical path to the same cuvette should be independent of the operation. Therefore, the priority of the consistency testing method is to measure any error caused by the front and back surfaces of the cuvette (because it is randomly inserted, both sides must be considered). The transparent surface of the cuvette is measured by the optical path and the transmittance of a given spectral segment. Strictly speaking, there are differences between the front and back transparent surfaces of the cuvette. Furthermore, the dust in the environment, non-standard operation or hand touch will lead to an error to a large extent.

So, error in the consistency of the device analysis is computed as:

$$\text{Error}(x) = Opt(x) - f(x)$$

Wherein x represents the detected component; f(x) represents the test result of a certain transparent surface of the cuvette; Opt(x) represents the test result of a single random operation of insertion; and Error(x) represents the error introduced by the pure operation that excludes the errors of the transparent surface of the cuvette itself.

$$f(x) = \text{Max}\left(\frac{1}{N}\sum_{n=1}^{N} \text{(The light transmission surfaces of } A \text{ and } B \text{ are continuously tested)}\right)$$

Wherein N represents the number of continuous measurements, A represents any of the transparent surfaces of the colorimetric dish, and B represents the other transparent surface of the colorimetric dish, which is turned by 180° from A.

$$Opt(x) = \text{Max}\left(\frac{1}{N}\sum_{n=1}^{N} \text{(actual operation of testing with the cuvette)}\right)$$

Wherein N represents the number of continuous measurements, and "actual operation of testing with the cuvette" means the whole process of inserting, testing, and extraction of the cuvette.

The consistency testing method only considers differences between results of each test and does not judge the accuracy of each test result. Since the principle of hyperspectral reflectance is used, the randomness of the analysis depends entirely on the structural design and assembly of the dark chamber. Compared with an atomic emission spectrometer, with which the atomic emission spectrometric method is used to gasify and plasmatize an oil sample by means of an arc excitation source, the disclosed method is more stable and predictable. According to experimental results, the consistency of the hyperspectral reflectance technology is in the range of 1-2% error.

Figure 9:
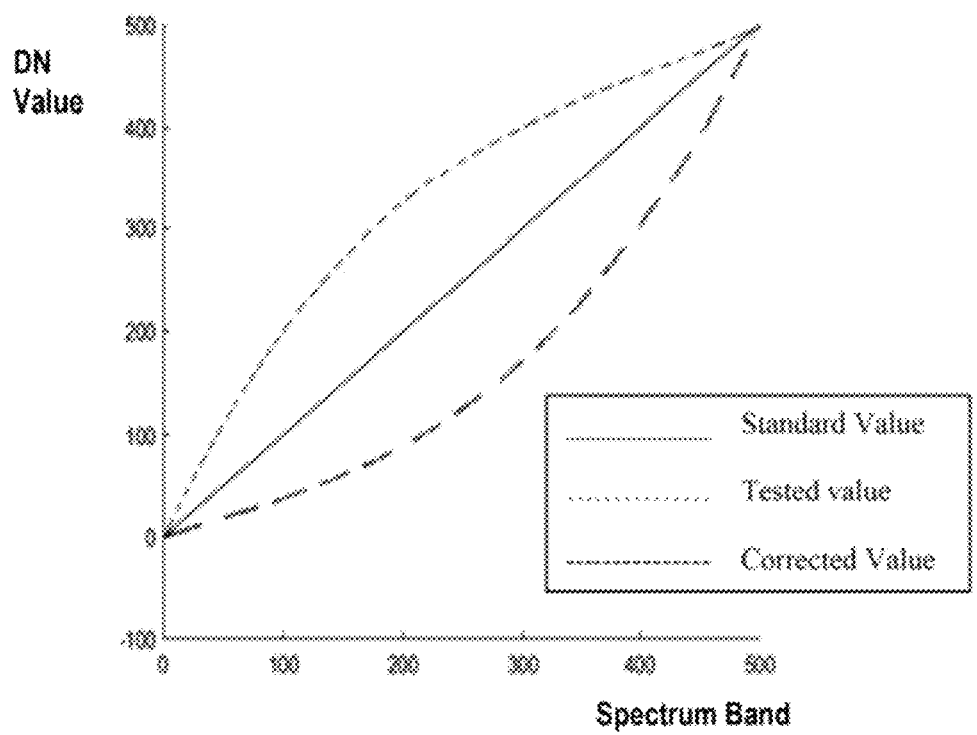
FIG. 9 is schematic diagram of how the calibration value is obtained according to the standard value and the detected value.

The calculated error for reflectance rate and DN value on each device should be used as a calibration (compensation) coefficient. Referring to FIG. 9, the three lines from top to bottom represent, respectively, 1) the reflectance rate and the DN value generated by daily operations, 2) the reflectance rate and the DN value collected and recorded for the standard optical plate when it is initialized, and 3) the calibration coefficient. The calibration is recorded and updated daily, and the reflectance rate and the DN value obtained from each operation of oil sample analysis on a day in question are multiplied by the corresponding calibration coefficient. Accordingly, the reflectance rate and the DN value of an oil sample that is pushed to the spectral model algorithm are made equivalent to the level of the initial state of the device. This method can effectively calibrate detection errors caused by components and/or environmental factors to maintain a "dynamic consistency" within a matter of seconds.

Developing System Database

The data processing and quantitative calculation algorithm inputs the spectrum (reflection frequency and DN value after splitting) of the oil sample being tested based on the spectral model parameters, and quantitatively calculates a detection result by partial least squares regression inversion. In practice, one-time model calibration is performed based on the actual oil sample of the application scenario and the laboratory test results. The present invention provides an efficient and implementable modeling method for spectral models, including benchmarking work for the model and actual oil types.

Modeling Method

Figure 13:
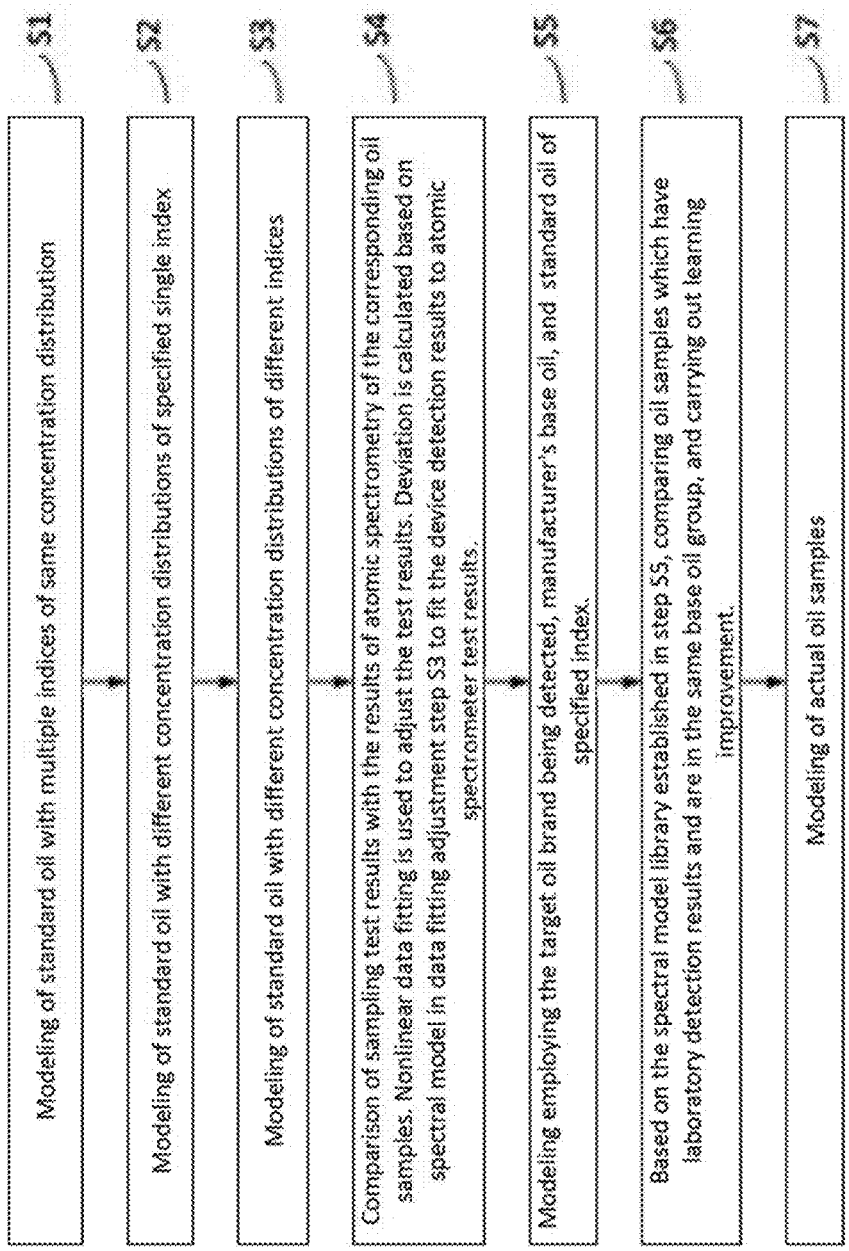
FIG. 13 is a flow chart of a modeling method for improving accuracy of hyperspectral lubricant analysis.

A spectral model is built from a set of oil samples that reflect changes in the oil in actual application scenarios. Oil samples used to build the spectral model should cover the entire life cycle of the oil in the equipment, such as the entire cycle of lubricating oil in rotating equipment from oil addition to oil replacement. Based on specific application scenarios, 20 to 30 oil samples are generally selected for modeling. In practical applications, this is the most effective and convenient way to achieve high-quality oil sample modeling and achieve test accuracy. But this approach is impractical. The present invention establishes a spectral model on the basis of the ideal state of a standard oil, assesses system accuracy independently of the oil samples and the spectral model, and achieves equipment accuracy under ideal conditions. Based on combined modeling of standard oil (components) and a target base oil (e.g., brand, manufacturer, grade), spectral models established with actual oil samples can be gradually increased. This is a workable method of achieving a targeted accuracy in a controllable, correctable, and iterative manner. Using this scheme, even if there is a degree of deviation in the detection results, a corresponding degree of correction can be achieved through mixed model. The framework and steps of the preferred process are set forth in the flow chart of FIG. 13.

Figure 3:
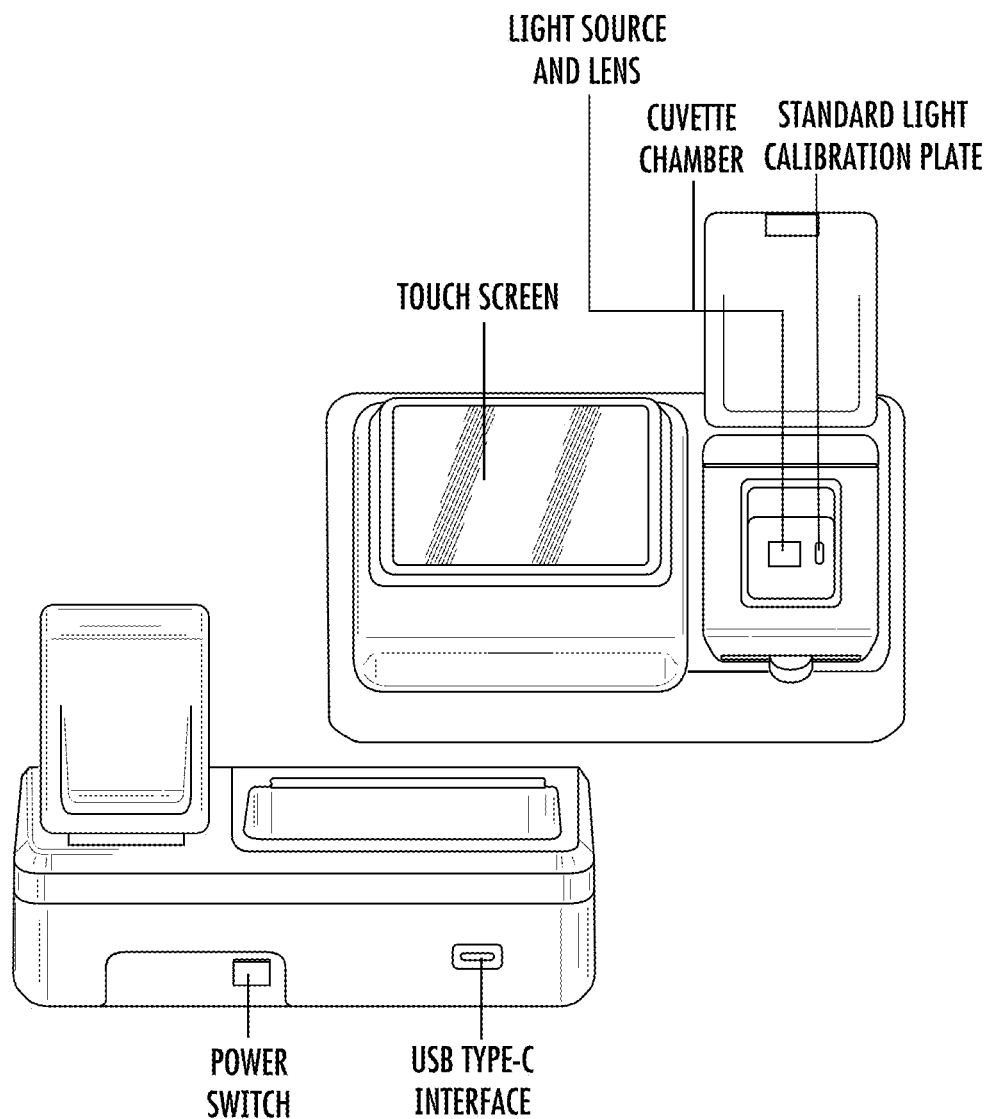
FIG. 3 is an embodiment of the device of FIG. 1B showing the top and backside of the device.
Figure 4:
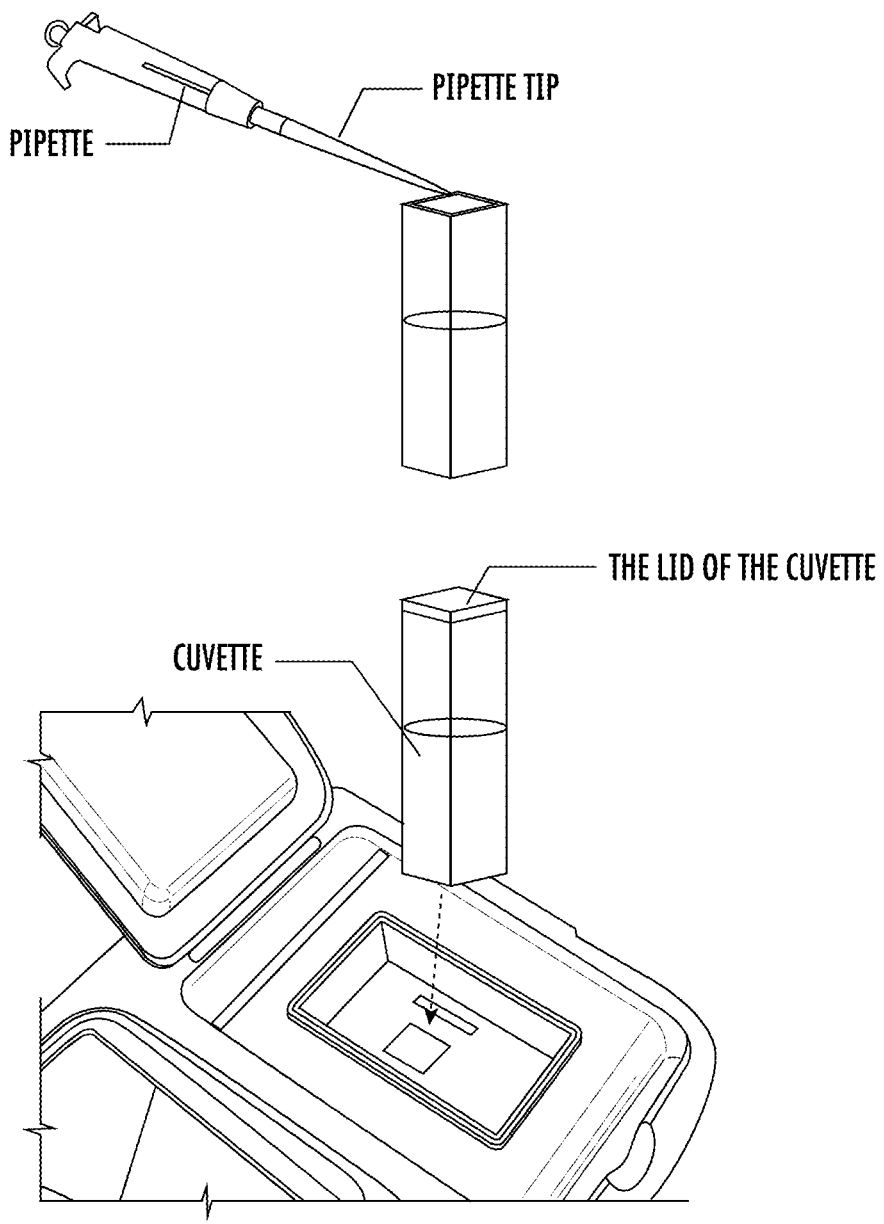
FIG. 4 is a partial image of the disclosed device showing a sample being added to a cuvette before insertion into the dark chamber.

Forming a closed loop of oil sample modeling, deviation correction, and improved accuracy can be used as a complement to the ideal approach (lacking practicality). The framework and steps of the scheme are shown in FIG. 3.

The lubricant oil analysis method based on reflected hyperspectrum disclosed herein is used for combining a model and actual oil types and comprises several critical steps.

S1: First, it is necessary to model standard oils with identical concentration distributions having multiple indices. By "standard oil" it is meant oil samples specially made by a company, typically in a lab, and certified by Officials. The oil samples are created by accurately controlling the concentration of an element (e.g., iron) put in each oil sample. These standard oil samples are used to calibrate test equipment in the company lab before the equipment is used to test actual oil samples obtained in the field. Standard oil for the present system and device were obtained from SCP Science (https://www.scpscience.com/en). Specifically, a webpage for such oil samples can be found using the following link: https://scpscience.com/en/products/categories?id=581&name=metallo-organic-standards-in-fuel-matrices.

This step is achieved by selecting a standard oil to be analyzed and obtaining, through dilution and calibration operations, a distributed standard oil group covering a preset spectral band, with a component distribution (e.g., ppm of metal) of the distributed standard oil group corresponding to different spectra. Then, it is necessary to establish multiple hyperspectral bands for the distributed standard oil group and a spectral model for a single known standard oil component index, with the spectral model being a parameter matrix.

The spectral model must then be tested, taking a hyperspectral band detected for the distributed standard oil group as an independent variable, incorporating the parameter matrix, and using the partial least squares method to achieve convergence and "test" output a dependent variable. The dependent variable would be the standard oil component index of the distributed standard oil group, which is capable of reflecting the distribution of components.

S2: Secondly, indices (i.e., the material in oil samples being analyzed) need to be specified and standard oils with different concentration distributions (i.e., ppm) need to be modeled. This is achieved by selecting a standard oil and—based on the known concentration and composition of the standard oil—using the dilution and calibration operations mentioned above to establish a spectral model covering the distributed standard oil group. Due to the different distribution of the component indices of the standard oil, the parameter matrix of this step will have one more component index dimension than the parameter matrix of the above step. Then, it is necessary to establish a standard test template based on the dilution method and the covered distribution, with the standard test template being a set of standard oil sample groups, and the index being close to the distribution of components in the actual oil sample. It is important to establish and test a hyperspectral model and spectral models of multiple known standard oil component indices of the hyperspectral model's standard test template.

Finally, an overall assessment of the accuracy of the spectral models, algorithms, and equipment is necessary, so that different equipment can meet the accuracy standards of the test template.

S3: Next, modeling the standard oil with different concentration distributions of different indices is required. This is done by selecting a standard oil, adding the indices and concentrations of the actual oil sample distribution in the application scenario, and repeating creation of different concentrations through dilution and calibration operations, as described above, to establish a distributed standard oil group covering the application scenario. Based on the distributed standard oil group created, multiple spectral models of known standard oil component indices can be created and tested. The application scenarios of the present invention include detecting metal components in oil, as well as macromolecular chemical (such as phosphorus and boron) components and physical characteristics (flash point, viscosity, particle size, and soot) in oil.

S4: Once the spectral models are created, it is necessary to sample the test results for comparison to laboratory produced atomic emission spectrometer detection results for corresponding oil samples (i.e., same indices and concentration). The detection results are then adjusted by nonlinear data fitting, and the calculated deviation of above created spectral models are adjusted based on the data fitting. Ultimately, the device detection results are fitted to the laboratory atomic emission spectrometer test results.

S5: At this point, modeling a target detection oil brand and the manufacturer's base oil combined with a specified index standard oil is required. Accordingly, a standard oil and a base oil in actual use are selected. Then, the dilution method described above is repeated to establish a distributed standard oil group, which is then conformed to the actual oil sample distribution in the application scenario, and a spectral model based on the distributed standard oil group is established and tested. Then, it is necessary to customize the standard oil by adding particles, mixing the same with an oil sample being tested, establishing a standard oil group with an actual oil sample distribution of samples to which particles have been added, and establishing and testing a spectral model based on the distribution of the standard oil group. The impact of particles on the spectral model (i.e., interference) can be evaluated and a corresponding anti-interference scheme devised. Ultimately, a spectral model database library can be created by establishing a series of spectral models for different base oils and standard oils of specified indices for different manufacturers and brands in conjunction with application scenarios.

S6: The accuracy of the library and system can be improved by comparing oil samples with the same base oil in laboratory test results.

Figure 26:
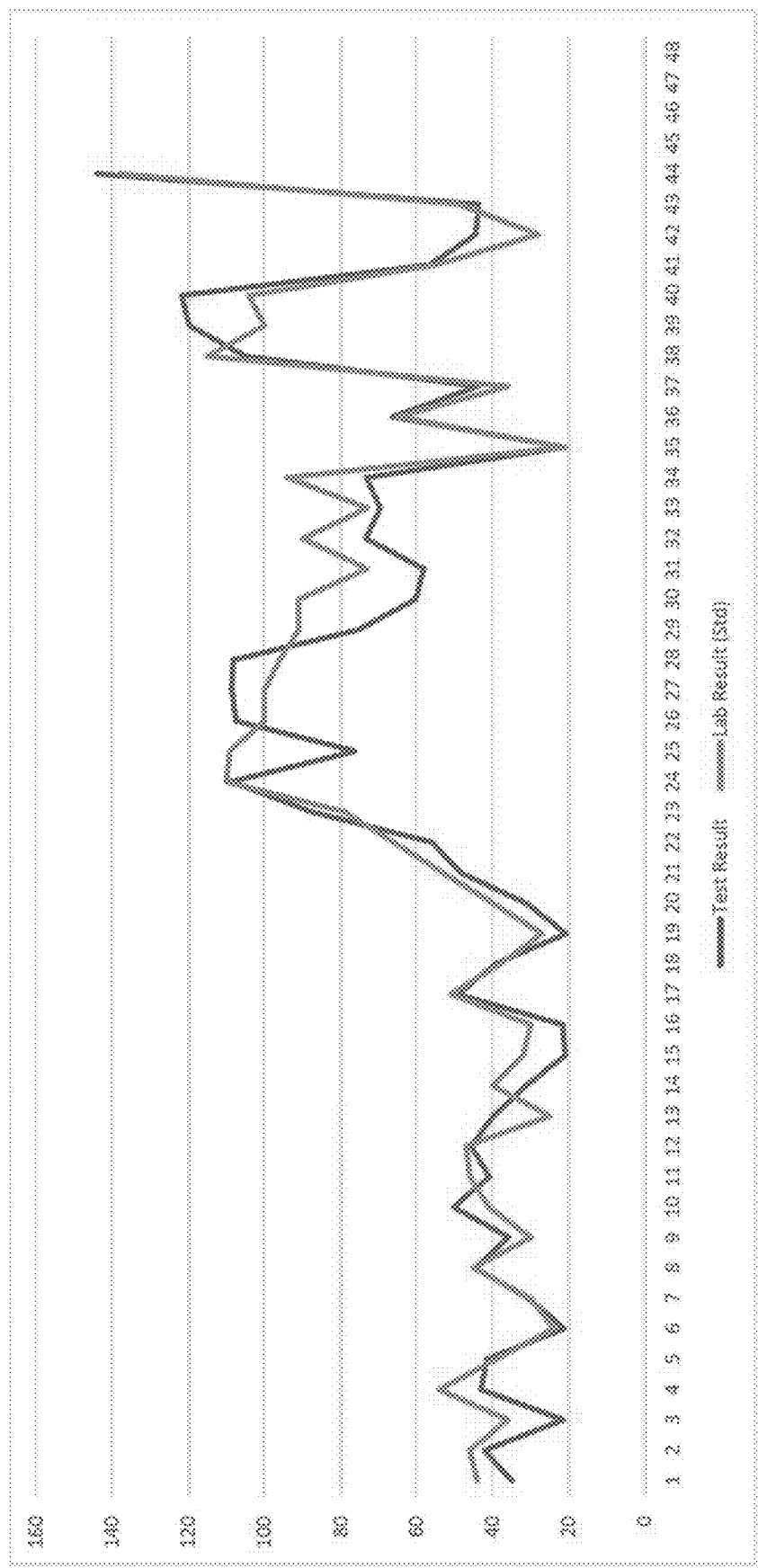
FIG. 26 is graph of data from TABLE 1 of the present disclosure.

S7: Finally, the actual oil samples are modeled using the base oil of an oil sample and a collected oil sample having the most concentrated components during an actual oil change. Using the dilution method described above, a distributed oil sample group is established which will cause the distributed oil sample group to conform to the actual oil sample distribution in application scenarios. A spectral matrix model is established and tested, comparing the oil samples with laboratory test results, as shown in TABLE 1 below (also see chart in FIG. 26), is used to improve accuracy.

TABLE 1

| No. | Cuvette ID | Test Result | Lab Result (Std) | Absolute Deviation | Relative Error |
|---|---|---|---|---|---|
| 1 | 3935 | 34.97808533 | 44 | 9.021914667 | 20.50% |
| 2 | 3937 | 42.1186854 | 46 | 3.8813146 | 8.44% |
| 3 | 3938 | 21.445459 | 36 | 14.554541 | 40.43% |
| 4 | 3942 | 43.0203084 | 54 | 10.9796916 | 20.33% |
| 5 | 3943 | 41.5673524 | 39 | 2.5673524 | 6.58% |
| 6 | 3945 | 21.1547244 | 24 | 2.8452756 | 11.86% |
| 7 | 3947 | 30.5606028 | 30 | 0.5606028 | 1.87% |
| 8 | 3948 | 44.751597 | 45 | 0.248403 | 0.55% |
| 9 | 3950 | 35.7415066 | 30 | 5.7415066 | 19.14% |
| 10 | 3951 | 50.2605548 | 41 | 9.2605548 | 22.59% |
| 11 | 3952 | 40.9071606 | 46 | 5.0928394 | 11.07% |
| 12 | 3954 | 45.660433 | 47 | 1.339567 | 2.85% |
| 13 | 3956 | 39.90236833 | 25 | 14.90236833 | 59.61% |
| 14 | 3957 | 31.1290464 | 40 | 8.8709536 | 22.18% |
| 15 | 3958 | 21 | 32 | 11 | 34.38% |
| 16 | 3959 | 21.54374083 | 30 | 8.456259167 | 28.19% |
| 17 | 3960 | 49.091045 | 51 | 1.908955 | 3.74% |
| 18 | 3962 | 39.431584 | 38 | 1.431584 | 3.77% |
| 19 | 3964 | 20.6711526 | 27 | 6.3288474 | 23.44% |
| 20 | 3965 | 31.2686812 | 40 | 8.7313188 | 21.83% |
| 21 | 3968 | 48.3643186 | 53 | 4.6356814 | 8.75% |
| 22 | 5357 | 55.7750995 | 66 | 10.22 | 15.49% |
| 23 | 5358 | 87.6220936 | 79 | 8.62 | 10.91% |
| 24 | 5359 | 108.6477237 | 110 | 1.35 | 1.23% |
| 25 | 5360 | 76.1848345 | 109 | 32.82 | 30.11% |
| 26 | 5364 | 107.3885956 | 100 | 7.39 | 7.39% |
| 27 | 5365 | 108.5204562 | 100 | 8.52 | 8.52% |
| 28 | 5367 | 108.2058254 | 96 | 12.21 | 12.71% |
| 29 | 5368 | 75.2757762 | 91 | 15.72 | 17.28% |
| 30 | 5370 | 60.2402322 | 91 | 30.76 | 33.80% |
| 31 | 5373 | 58.08164267 | 73 | 14.92 | 20.44% |
| 32 | 5374 | 73.2745005 | 90 | 16.73 | 18.58% |
| 33 | 5375 | 69.5283086 | 73 | 3.47 | 4.76% |
| 34 | 5380 | 73.16164767 | 94 | 20.84 | 22.17% |
| 35 | 5529 | 21.01300633 | 21 | 0.01 | 0.06% |
| 36 | 5530 | 66.3806032 | 65 | 1.38 | 2.12% |
| 37 | 5531 | 43.88358167 | 36 | 7.88 | 21.90% |

TABLE 1-continued

| No. | Cuvette ID | Test Result | Lab Result (Std) | Absolute Deviation | Relative Error |
|---|---|---|---|---|---|
| 38 | 6032 | 105.0048356 | 115 | 9.9951644 | 8.69% |
| 39 | 6033 | 119.7791534 | 100 | 19.7791534 | 19.78% |
| 40 | 6034 | 121.7734986 | 104 | 17.7734986 | 17.09% |
| 41 | 6036 | 56.59071283 | 55 | 1.590712833 | 2.89% |
| 42 | 6038 | 44.41600733 | 28 | 16.41600733 | 58.63% |
| 43 | 6041 | 43.7198786 | 49 | 5.2801214 | 10.78% |
| 44 | 0565 | 143.9999906 | 138 | 5.9999906 | 4.35% |

In all instances, the "Absolute Deviation" (i.e., Test result—Lab Result) is less than required by ASTM D5185, satisfying lab ICP-AES equipment test results. ASTM D5185 is used as a verification standard as it is an international standard for lab equipment.

Figure 14:
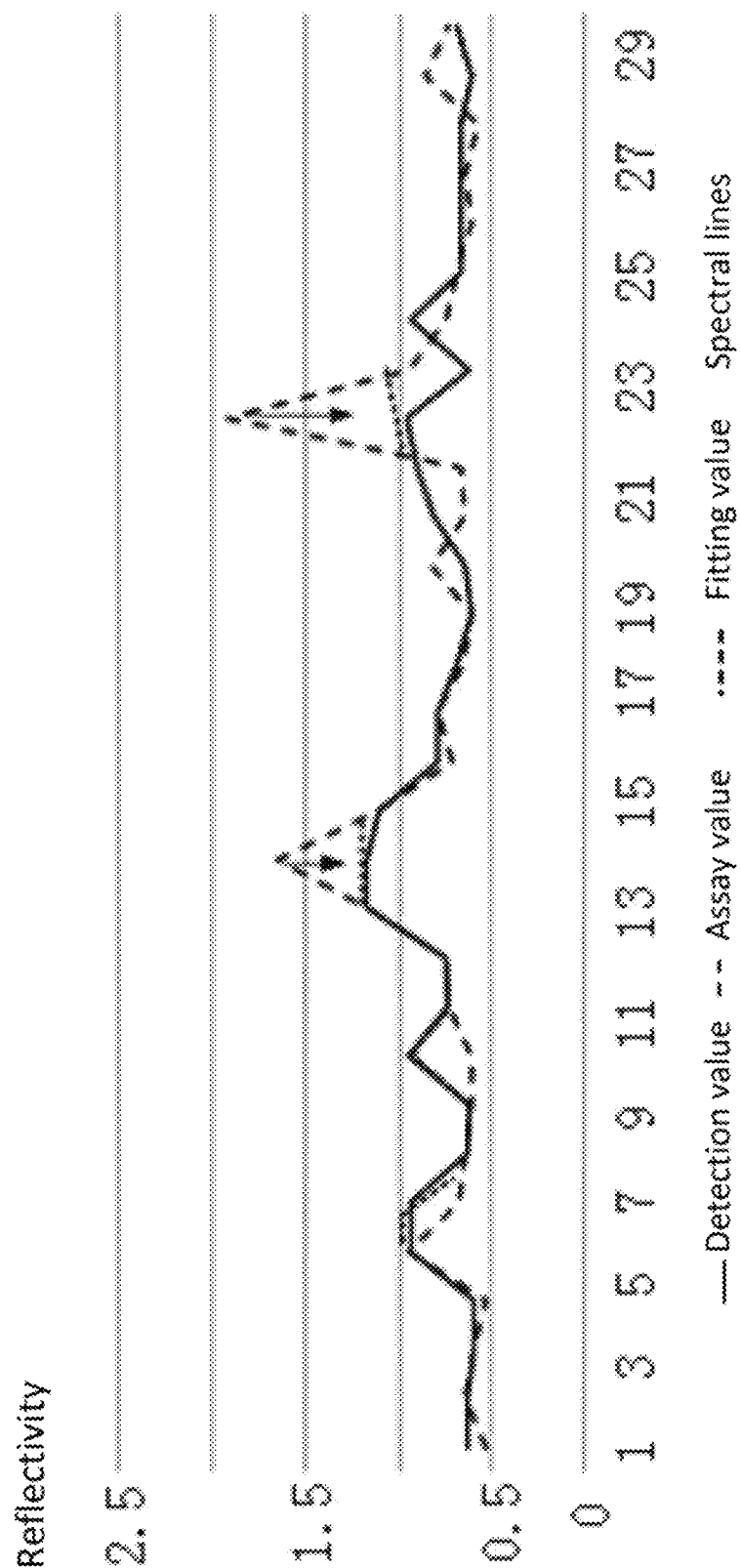
FIG. 14 is a schematic diagram of actual oil sample modeling (assay value curve) errors when fitting to a combined model (detection value curve)

FIG. 14 is a diagram of the modeling errors of actual oil samples corrected by combined model fitting. Therein, the detected value (solid line curve) is the modeling test result in step S6 above, which is used to correct the modeling error of the actual oil samples. The assay values (curve marked by long dashes) are the actual sampling modeling results. The arrows indicate the correction targets, and the short-dash line indicates the results of convergence fitting by the partial least squares algorithm.

Field Testing—Overall Process

Once a model for the application scenario is established, and the oil sample being tested is inputted into the system, field testing can be performed. The first step is to select the oil type of the oil sample being tested—i.e., the target brand manufacturer's base oil—and determine a hyperspectral model. The oil sample to be tested is collected and manipulated by a hyperspectral oil detector to form a set of reflectivity and DN value spectra, which are inputted for detection. Spectral band splitting and processing segments are also required. The spectral bands of a specified element in the oil sample being tested are calculated based on the precise spectral segment of a characteristic spectral band of the specified element provided by the hyperspectral model library as an objective function. Generally, over the entire element spectrum (400 nm to 2,300 nm) several spectral bands (generally between 400 nm and 1,000 nm) are selected, based on experience. The number of spectral bands corresponds one-to-one with the spectral models. Upon accurately acquiring a spectral λ band (set), the value of the band (denoting an elemental component density) will necessarily form a corresponding relationship with a specified element spectral band of the hyperspectral model for the oil type. The partial least squares method is used to analyze the statistical relationship between the dependent variable and the independent variable. The stepwise process of the partial least squares method is as follows:

1. Establishing a residual information (remaining information) matrix $E_0$ and a detected oil sample component matrix $F_0$, where $E_0$ is a standardized independent variable matrix, each row is a series of component indices, and each column denotes a set of spectral variables corresponding to the detected element indices. $F_0$ is a dependent variable matrix. Similar to $E_0$, each row is a series of component indices, and each column denotes a set of spectral band variables corresponding to the detected element indices. Data normalization consists of subtracting the mean of each spectral band and then dividing by the standard deviation of each spectral band;

2. Solving for the eigenvector $w_1$ corresponding to the maximum eigenvalue of the matrix $E_0^T F_0 F_0^T E_0$ to obtain a component score vector $\hat{t}_1 = E_0 w_1$ and a residual information matrix $E_1^T = E_0 - \hat{t}_1 a_1^T$, wherein $a_1 = E_0^T \hat{t}_1 / \|\hat{t}_1\|^2$;

3. Solving for the eigenvector $w_2$ corresponding to the maximum eigenvalue of the matrix $T_1^T F_0 F_0^T E_1$ to obtain a component score vector $\hat{t}_2 = E_0 w_2$ and the residual information matrix $E_2 = E_1 - \hat{t}_2 a_2^T$, wherein $a_2 = E_1^T \hat{t}_2 / \|\hat{t}_2\|^2$;

4. Repeating the above steps to the $m^{th}$ step and solving for the eigenvector $w_m$ corresponding to the maximum eigenvalue of the matrix $E_{m-1}^T F_0 F_0^T E_{m-1}$ to obtain a component score vector $\hat{t}_m = E_{m-1} w_m$;

5. Based on cross validity, determining that a total of m components $t_1, t_2, \ldots, t_m$ have been extracted to obtain a prediction model; solving the common least squares regression equation for $F_0$ on $t_1, t_2, \ldots, t_m$:

$$F_0 = \hat{t}_1 \beta_1^T + \hat{t}_2 \beta_2^T + \ldots + \hat{t}_m \beta_m^T + F_m$$

wherein $\beta_1, \beta_2, \beta_m$ denote the weighting parameters of the $1^{st}$, $2^{nd}$, and $m^{th}$ components, respectively, and Fm denotes the residual information matrix after extracting m components. In certain of the embodiments, $\beta_1$ may be the weighting parameter of the element iron, and $\beta_2$ may be the weighting parameter of the element manganese. The present invention makes no limitation in this regard.

If data tables X and Y are subjected to m components ultimately extracted for X, substituting $t_k = w_{k1} * x_1 + w_{k2} * x_2 + \ldots + w_{kn} * x_n (k=1, 2, \ldots, m)$ into $Y = t_1 \beta_1 + t_2 \beta_2 + \ldots + t_m \beta_m$ to obtain the partial least squares method regression equation of p dependent variables:

$$y_j = a_{j1} x_1 + a_{j2} x_2 + \ldots + a_{jn} x_n (j=1,2,\ldots,p)$$

such that here $w_h^* = (w_{h1}^*, w_{h2}^*, \ldots, w_{hn}^*)^T$ satisfies $\hat{t}_h = E_0 w_h^*$, $$w_h^* = \Pi_{j=1}^{h-1}(I - w_j a_j^T) w_h$$

The objective function is:

$$\min \|y_j - \delta_1 a_{j1} x_1 - \ldots - \delta_k a_{jk} x_k - \delta_n a_{jn} x_n\| + \left\| tr(w_h^{*T} E_0 w_h^*) - tr(\hat{t}_h E_0 \hat{t}_h^T) \right\|,$$

wherein $$\delta_k = \frac{1}{1 + \left|\frac{L_{DN}(\lambda_k) - \overline{L}_{DN}}{\overline{L}_{DN}}\right|},$$

$$j = 1, 2, \ldots, p$$

with $L_{DN}(\lambda_k)$ being the $k^{th}$ band radiance value and $\overline{L}_{DN}$ being the band average radiance value, and with the constraint condition being: $a_{j1} > 0, \ldots, a_{jk} > 0, a_{jn} > 0$.

Usually, the dependent variable Y is the detected index (element component) that needs to be inverted (calculated or reconstructed). The partial least squares method makes it possible to calculate multiple detection indices. Here Y can be multi-dimensional detection index data. For example, it can be the amount of metal dust and chemical components in the oil being tested. A rigorous relationship is established between the detected index of the inversion result and the corresponding hyperspectrum. The detected index and the actual index concentration of the detected oil are calibrated to quantitatively estimate the element component content of the oil.

The partial least square regression algorithm described above is used to build a model and compute using independent variables (e.g., reflectance and DN value) and dependent variables (e.g., indices). The fold interleaved method is used to re-learn the inputs (reflectance and DN value) based on the existing model with a subset of known samples based on dilution distribution points (i each sample created by gravity method) to improve the system accuracy.

The description of the algorithm is part of the folded interleaved verification method (for re-learning of the model purpose). The partial least square convergence of the above steps (for building the model) is to use the maximum eigenvalue of the matrix at each iteration (as described above). These steps are preferably repeated "i" times, $1 < i < K$, K: the number of oil sample dilution distribution points (starting from 0), each time using a different training set and test set (different gradients of oil sample dilution distribution). Depending on the number of iterations the model is trained on, the predicted value will approach the output of the model training set.

The overall test mean square error (MSE) is calculated as the average of K test MSEs, or:

$$MSE = \frac{1}{K} \sum_{i=1}^{K} MSE_i$$

Ordinarily, the larger the number of iterations used in the K-iteration cross-refinement model is, the lower the deviation of the observed test MSE is (the difference between the predicted value and the model training set) but the higher the variance is. The "variance" is folded into the model by the system's own interference (noise). Conversely, the fewer iterations used, the higher the deviation, but the lower the variance. In practice, the selection is made based on the gradient variation of the oil sample being modeled and the characteristics of the actual sampling point. This choice has been shown to provide the best balance between deviation and variance, thereby providing a reliable estimate of the test MSE, enabling re-learning of the model and improving the relative accuracy of the test.

The specific steps of the volume specific gravity method are as follows:

Using the method of simply weighing and diluting the oil, the base oil and the test oil sample with laboratory test results are diluted based on a predetermined concentration gradient. This is characterized by simple operation, no need for laboratory equipment or environment, rapidity, accuracy (no cumulative error), no consumption of test oil samples (or base oil), and the like. It is an important link in implementation of the folded interleaved verification method, as well as in satisfying the accuracy of the training set and the test set. The operation process requires only auxiliary equipment: an electronic balance (specification: Max=200 g, e=0.01 g, d=0.001 g), two test tubes with 10 mL markings (including a stand for the test tubes to stand upright), and a pipette. The operation process assumes that the cuvette and cuvette holder required by the hyperspectral oil testing equipment to detect oil samples are present.

The primary method is as follows:

1. Obtaining the unit specific gravity of the base oil and an oil sample with laboratory test results. The specific gravity of the oil sample can be calculated by charging 10 mL of the oil sample into a test tube and calculating the weight difference (subtracting the weight of the test tube).

2. Obtaining the weight of the test oil sample and the base oil that require dilution in the cuvette (3.4 mL). The weight of the oil sample to be charged to a 3.4 mL cuvette can be calculated from the weight of two 10 mL oil samples (using the results of step 1) (mixing the two oil samples).

3. Calculating the weight of the base oil and the weight of the test oil sample to be separately charged to the cuvette based on the dilution point. The calculation method may be simplified as, $$x_{oil\,sample\,tested} = \frac{W_{cuvette} * \text{target dilution concentration}}{\text{component being detected}}$$

Wherein "$x_{oil\,sample\,tested}$" is the weight of the oil sample being tested to be introduced based on the target dilution concentration, $W_{cuvette}$ is the weight of the oil sample to be charged to the cuvette (obtained from step 2 above), and the target dilution concentration is the dilution point of the oil sample relative to the accompanying laboratory test results (for example, the relative targeted component is diluted from 200 ppm to 20 ppm). The component being tested is the target component (for example, iron Fe) in the sample being tested in the accompanying laboratory test results.

The weight of the base oil to be added to the cuvette: $W_{cuvette} - x_{oil\,sample\,tested}$.

An electronic balance is employed. The cuvette is placed in a holder, which is then placed on the balance to obtain the net weight. Using a pipette, the test oil sample and the base oil are introduced based on the weights of the test oil sample and the base oil calculated in step 3 to reconstruct a test oil sample at the dilution point.

Oil Samples

In some embodiments, the specific steps and material used for creating oil samples are as follows:

S1: Modeling of standard oil with the same concentration distribution of different indices. Taking the standard oil produced by SCP Science as an example, the specifications are as follows:

| Specification model number | Description |
|---|---|
| 150-075-002 | CONOSTAN 75 cSt Blank Oil with certificate |
| 150-021-598 | CONOSTAN S-21 900 ppm 24 elements, each element in a concentration of 900 ppm: 24 elements of Ag Al B Ba Ca Cd Cr Cu Fe Mg Mn Mo No Ni P Pb Si Sn Ti V Zn with additional K Li Sb |

Through dilution and calibration operations, establishing a distributed standard oil set ranging from 0 to 900 ppm. Modeling and testing. Measuring the accuracy that can be achieved by the equipment and advancing to the next step once the absolute error, accuracy, relative error, and so on have been satisfied the specified conditions.

S2: Modeling of standard oil with different concentration distributions of specified indices. Taking the standard oil produced by SCP Science as an example, the specifications are as follows:

| Specification model number | Description |
|---|---|
| 150-075-002 | CONOSTAN 75 cSt Blank Oil with certificate |
| CB0-009-628 | CONOSTAN customized standard oil sample nonuniform metal content configuration: Sn 200 ppm, Pb 250 ppm, Ni 300 ppm, Cu 350 ppm, Cr 400 ppm, Al 450 ppm, Fe 500 ppm |

Through dilution and calibration operations, establishing a distributed standard oil set ranging from 0 to 200 ppm by using Fe concentration as the reference. Modeling and testing. The standard test template, including dilution method and coverage distribution, performs a general assessment of the accuracy of the spectral model, algorithm, and equipment that satisfies step S1 above. The absolute error is required to be less than 10% (accuracy 2 ppm), and the relative error is within 2%.

S3: Modeling of standard oil with different concentration distributions of different indices. Taking the standard oil produced by SCP Science as an example, the specifications are as follows:

| Specification model number | Description |
|---|---|
| 150-075-002 | CONOSTAN 75 cSt Blank Oil with certificate |
| CB0-009-748 | CONOSTAN customized single component standard oil sample (metal content configuration): Fe, Mg, Cr, Cu, Zn, silicon, boron. Content configuration of 300 ppm. |

Combined with the actual oil sample distribution in the application scenario, a distributed standard oil group is established ranging from 0 to 200 ppm. Modeling and testing.

S4: Comparison of sampling test results with atomic spectrometer detection results (corresponding to oil samples) and adjusting the model so that the test results of the equipment are fitted to the test results of the atomic spectrometer. Using the hyperspectral model detection results to calibrate the laboratory detection results. This step establishes the hyperspectral model detection and correction mechanism (parameters) of the laboratory detection equipment. An atomic spectrometer is a type of laboratory equipment, and as a supplemental verification tool in the present invention, this step needs to be conducted in a laboratory.

S5: Modeling by combining the target brand manufacturer's base oil and the specified index standard oil. Taking the standard oil produced by SCP Science and combining it with the base oil in a real application scenario as an example, the specifications are as follows:

| Specification model number | Description |
|---|---|
| Base oil | Based on application scenario: different manufacturer, brand |
| CB0-045-326 | CONOSTAN customized single component standard oil sample (metal content configuration): Fe, Mg, Cr, Cu, Zn, Ti; phosphorus, silicon, boron. Content configuration of 300 ppm. |

By combining the actual oil sample distribution in the application scenario, a distributed standard oil group is established by the dilution method, ranging from 0 to 200 ppm. Modeling and testing. Adding particles (can also be introduced through customized standard oil), mixing with the oil sample to be tested (if standard oil is used, step S3 is repeated, and Blank Oil is replaced by base oil), and performing modeling and testing. Evaluating the interference of particle size on the spectral model and the corresponding anti-interference scheme. Standard oil is modeled through different base oils and specified indices (combined with application scenarios to detect components), and a model library combined with application scenarios is established. The system software automatically retrieves and switches models in conjunction with its operating logic. The goal is to render the operation as simple as possible for users, such as operators. For example, there is no need to know the manufacturer or brand of the lubricating oil sample being tested.

Figure 15:
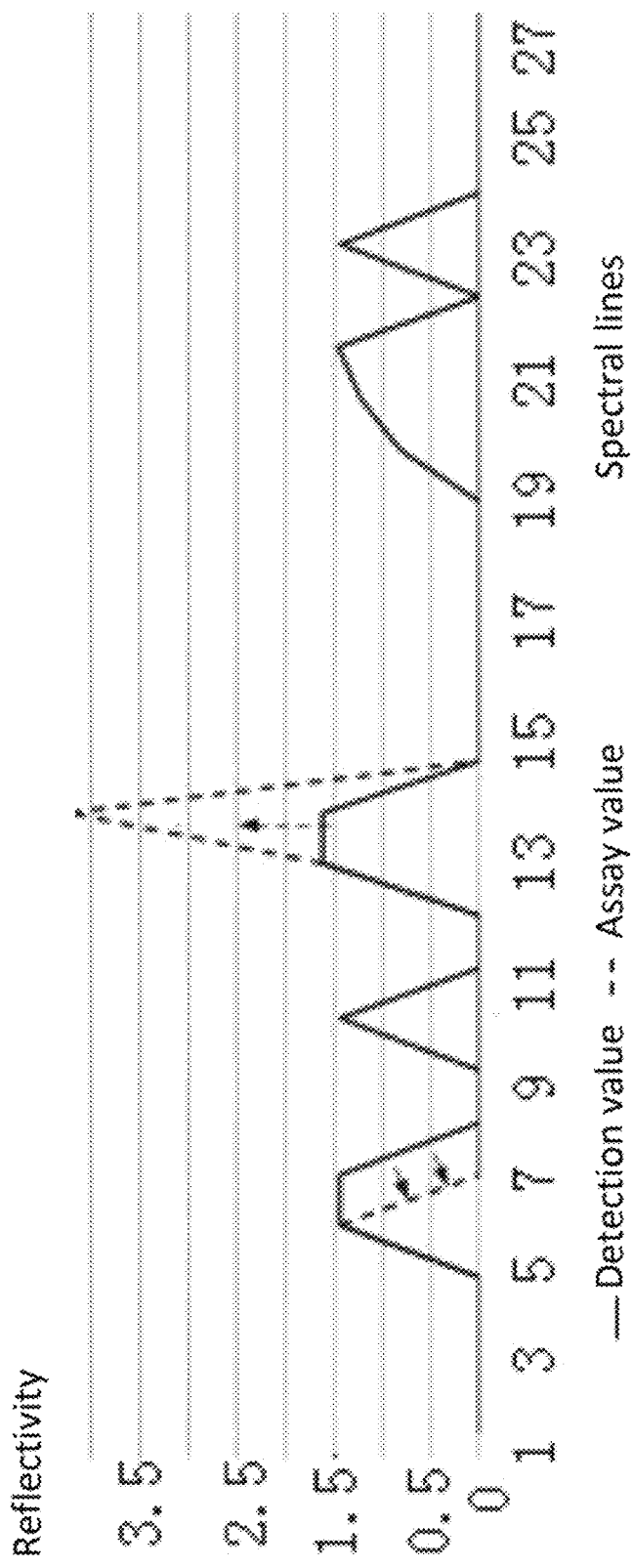
FIG. 15 is a schematic diagram showing combined modeling to achieve partial improvement in accuracy—the detection value curve is the result of model testing, and the assay value curve is the result of actual sampling laboratory detection.

S6: Based on the model established in step S5 above, carrying out "learning" improvement (combination modeling) by means of the same base oil sample with laboratory test results. As shown in FIG. 15, based on the number of oil samples, the detection accuracy of the model for the actual oil samples can undergo a transitional (or partial) improvement process. A calibration model can be provided for modeling with pure real oil samples of the same oil product; the specific steps are described in step S7 below.

In the figure, the detection value (solid line curve) is the modeling test result in step S5 above. The assay value (dashed curve) is the actual sampling laboratory test result, and the arrows indicate the calibration targets.

S7: Modeling of actual oil samples. The base oil of the oil samples and oil samples collected during actual oil changes (of relatively concentrated composition) are used. These are combined with the actual oil sample distribution in the application scenario, and a distributed oil sample group is established by the dilution method. Modeling and testing. If there is a difference in accuracy, step S6 above is combined to improve the accuracy by combining models. This is shown in FIG. 14.

As shown in Table 2 below, compared to prior art the advantages of the present invention are numerous, including being lighter, more versatile, faster, and less wasteful.

The present invention simplifies the operating sequence under specified application scenarios (having a spectral model), and obtains detection results conveniently, quickly, on the spot, and in real time.

Specific Embodiment

U.S. Pat. No. 11,650,145 (application Ser. No. 17/396,986), previously incorporated by reference, describes an early conceptual version of the system, aspects of which are relevant to the preferred embodiment of the present system. That earlier conceptual embodiment is described with reference to FIGS. 20-25. In these figures there is illustrated a system and method for remote hyperspectral sensing and analysis of fluid samples. The disclosed system includes a portable, battery-operated, remote, hyperspectral sensing instrument, generally indicated by the numeral 11. As shown, the instrument 11 comprises a light source (emitter) 14, a light detector (receiver) 15 and spectral splitter 16, and a photoelectric converter 17. The instrument 11 is connected to a data processing unit 120, via wireless transmission using the Internet and a Cloud-based server 122.

Using the portable instrument 11, the system can calibrate and match data by a hyperspectral model and output data corresponding to a composition of any material in a liquid sample (e.g., metal elements). The sample testing can be done onsite with results in a relatively short period of time. The output data can be formatted as a report providing diagnostic information, recommendations, and/or merely calling attention (i.e., alerts) to the sample and providing application scenarios.

The system is primarily comprised of instrument 11, which connects to the Cloud-based server 122. The instrument consists of acquisition peripherals, hyperspectral acquisition, processing and transmission, and result display.

TABLE 2

| Performance Comparison | Device Characteristics | Weight (Kg) | Analysis Content | | | | |
|---|---|---|---|---|---|---|---|
| | | | Metal Composition | Other* | Flash Point | Operation Time | Consumables |
| QSAD | Portable (battery driven lasts 24 hours) | 1 | Yes | Yes | Yes | 5-6 sec | Low |
| Spectroil 100 (USA) | Desktop (Lab Equipment) | 75 | Yes | No | No | 30 sec | High |
| FieldLab 58 (USA) | Portable (battery driven lasts 4 hours) | 15 | Yes | Yes | No | 5-7 min | High |
| MicroLab 40 (USA) | Desktop (Lab Equipment) | 59 | Yes | Yes | No | ~15 min | High |

*Other: Chemical composition, particle size, viscosity

The present invention can establish multiple models for metal components or macromolecular chemical components and can simultaneously detect metal components and macromolecular chemical components.

The product of the present invention does not require a vacuum dark chamber, extracts atomic spectral bands by mathematical methods, and simplifies the structural design, process, and consumables of the atomic excitation light source. By modeling the oil range to be detected and inferring a measurement algorithm, the requirements for the spectral band range are reduced, dependence on the extreme ultraviolet spectral range is avoided, and the complexity of the spectral system is greatly reduced. It is portable, low-cost, real-time, and intelligent, and is thus compact and consumables-free.

The Cloud-based server 122 consists of an information platform, calibration and processing, hyperspectral model matching, application driven expert system, measure result and diagnosis.

In addition to the instrument 11, acquisition peripherals include equipment such as a sample container 13 with an NFC chip to hold about 1.6-2.0 ml lubricant oil sample and its electronic unique ID (UID), a black and white standard reflection board for calibration, an acquisition base (i.e., create a dark environment) to support the system during acquisition, and a lens' hood 12. The system registers the sample container UID in a database and binds the container with a point of inspection (engine or rotary equipment) where oil type is known through a QR code sweep gun (not shown). The instrument 11 is able to connect the oil sample with the Cloud-based server 122 during test operation, so the right Hyperspectral Model can be used to match, and results can be transmitted to the instrument 11, and stored in the database.

Figure 20:
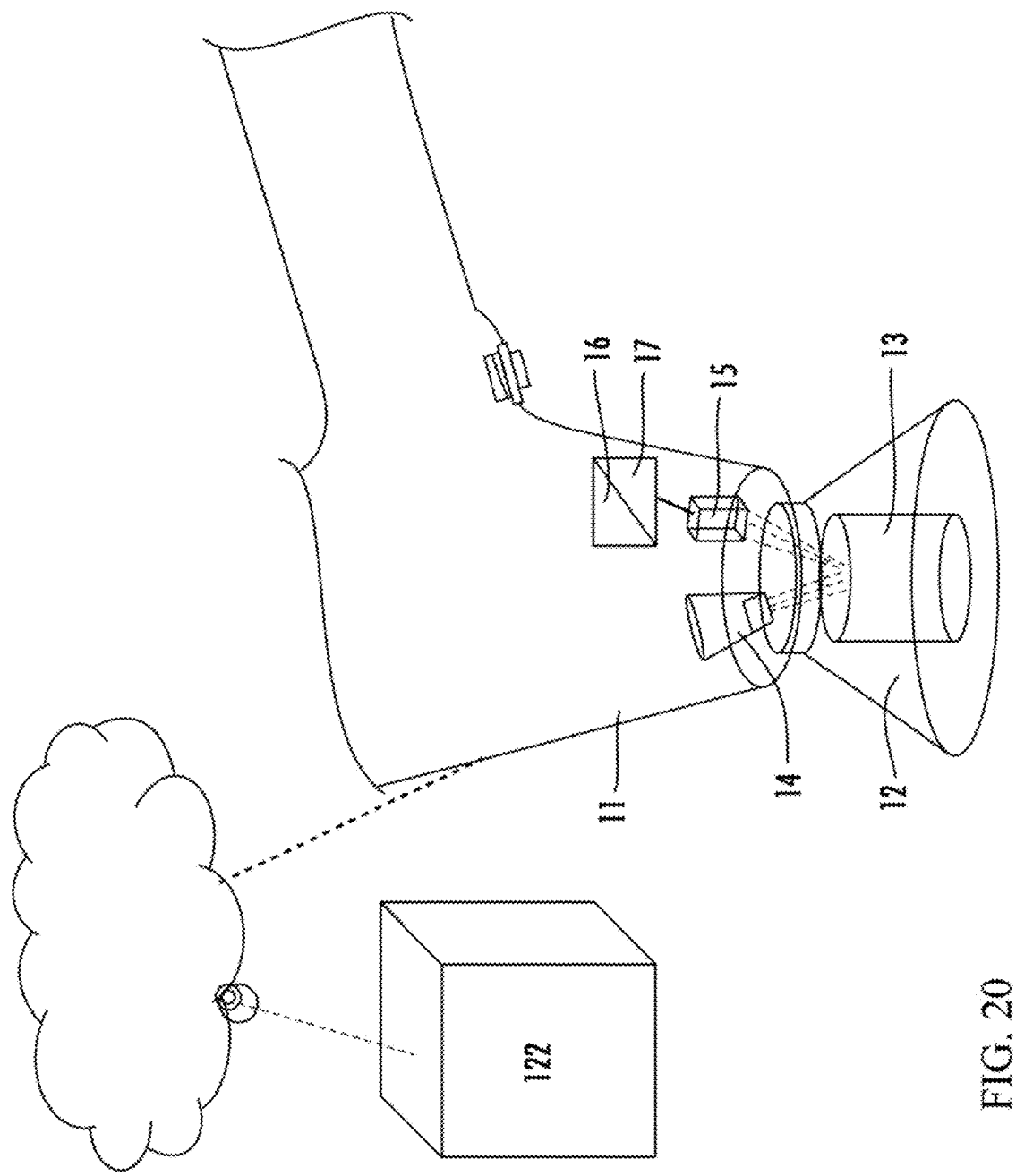
FIG. 20 illustrates an embodiment of a hyperspectral sensing instrument and its peripherals.

The hood 12, as shown in FIG. 20, is used to make sure operation is consistent and independent from human involvement and keeps "light noise" low by keeping the light source as uniform for each acquisition as possible.

Figure 21:
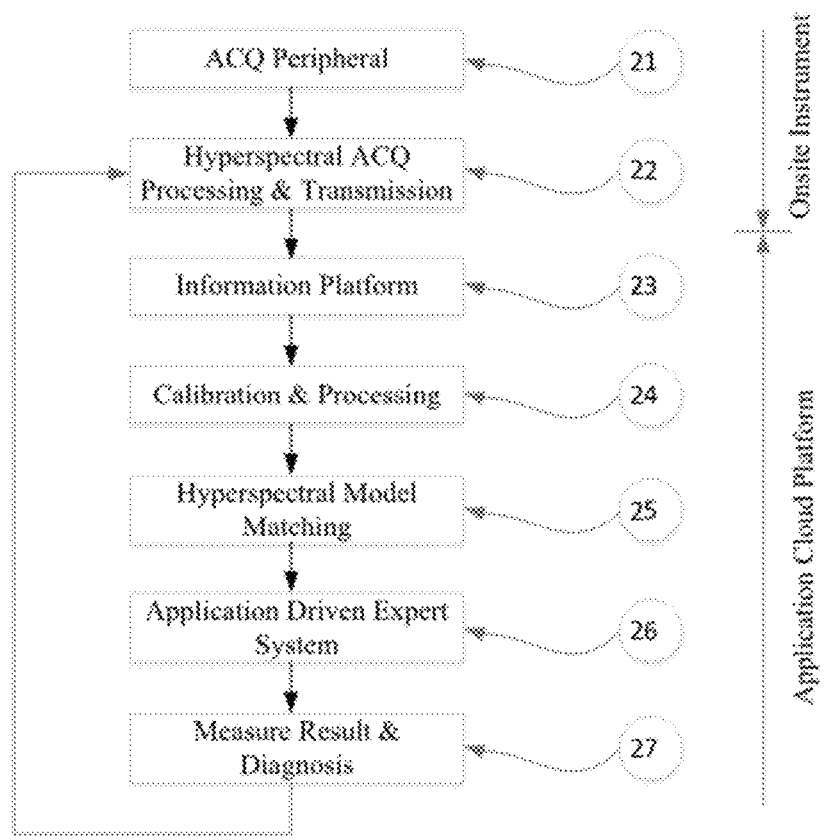
FIG. 21 is a process flowchart of an embodiment of the disclosed system.

With reference to FIG. 21, the following defines some terms and describes embodiments of specific components used in the disclosed system.

Acquisition Peripheral 21. This component provides equipment such as a sample container, with NFC chip to hold lubricant oil sample and its ID, a black and white standard reflection board for calibration, an acquisition base (dark environment) to support the instrument during acquisition, a lens' hood to make sure the system produces consistent acquisition data independent from every operation.

Hyperspectral Acquisition, Processing and Transmission 22. This process describes the functions provided by the instrument. For example,
   a. It preferably uses a halogen light source to produce a uniform and smooth emission line form hyper-spectrum with a characteristic wavelength (band) of 400-1000 nm;
   b. It uses a detector to form an angle from the light source to maximum reflection acceptance;
   c. It uses a hyperspectral splitter after the detector to segment acquired spectrum band width with 3 nm resolution into 200-300 intervals (bands);
   d. It runs through a photoelectric converter in each individual band to generate reflection and DN values. respectively;
   e. It combines results of all intervals, forms two data series with band intervals as horizontal axis, called "two curves";
   f. It uses 4G to transmit the two curves to the dedicated the Cloud-based server; and
   g. It displays the element contents, element traced curve, and recommendation information, received from the Cloud-based server.

Information Platform 23. This component responds to setup a connection channel between an instrument and the Cloud-based server which facilitates an application driven platform dedicated for the end user.

Calibration and Processing 24. This component responds to measure the instrument and acquisition environment and compares to its initialization setting, use difference to generate compensation value for each band, applies them during each acquisition to offset the system errors and make sure the acquisition data consistent and stable.

Hyperspectral Model Matching Processing 25. This feature is comprised of two distinct procedures. First, the process is tasked with building a Hyperspectral Model based on a given number of oil samples with laboratory test results. A proprietary data processing method is used as well as a Hyperspectral Library to build the Hyperspectral Model (see detail illustrated in FIG. 23). Second, the process calculates the acquisition oil sample testing results through a Hyperspectral Model matching process. The proprietary data processing method and Hyperspectral Model are used to calculate the results (see detail illustrated in FIG. 24).

Application Driven Expert System 26. This component uses application domain knowledge applied to the test results and provides meaningful information to less skilled onsite users to obtain mission critical maintenance diagnosis and recommendation in seconds. It is based on data accumulation and lubricant oil information to reconstruct a new (or updated) Hyperspectral Model for precision improvement and measurement expansion.

Measure Results and Diagnosis 27. This component responds to store, display, and trace the results. It also provides data management and authorization for distribution.

As previously noted, the hyperspectral sensing instrument 11 produces a uniform and smooth emission line with a characteristic wavelength (band) of 400-1000 nm. The composition of any dissolved material, metal elements, in the lubricant oil sample will have a different reflectivity of light at different wavelengths (bands) between 400 and 1000 nm. The reflectivity is detected by the instrument. Each element can be represented by a reflection value and a digital number (DN), as a function of the different wavelength bands. The reflection value and DN are as follows:

$$\text{Reflection} = f_1(\text{band})$$

$$DN = f_2(\text{band})$$

The detector 15 on the instrument 11 forms an angle with the light source 14 to maximize reflection acceptance. A hyperspectral splitter 16 after the detector 15 is used to segment the acquired spectrum with about 3 nm resolution or band widths. As a result, the splitter 16 divides the spectrum into about 200 to 300 distinct bands. Each individual band runs through a photoelectric converter to generate the reflection and DN values. By plotting the results of all the individual bands, two curves are formed based on the formulas above. Using broadband cellular network (4G or greater), the two curves are transmitted to a dedicated Cloud-based server 122. To summarize the process of Hyperspectral acquisition above, each acquisition operation emits hyperspectral light to the substance, receives reflection spectrum, splits the spectrum into distinct bands, converts the reflectance into two numbers, generates two curves based on the two numbers at each band and broadcasts the two curves to the Cloud-based server for storage.

The information platform 23 indicated in FIG. 21 is the gate of the Cloud-based server 122. It communicates onsite with the instrument 11 and the processing units in the Cloud-based server. In addition to the instrument ID, lubricant oil sample container ID—in which the type of lubricant oil, oil sample collection time, instrument internal temperature, etc., can be sorted from the system—and hyperspectral acquisition data (i.e., the two curves) are transmitted to the Cloud-based server. The Information platform 23 uses the instrument ID to verify attribution and legitimacy and set communication channel for return testing results. The information platform 23 also plays a connection role and is able to expend itself to handle hundreds of instruments to conduct testing at the same time.

The calibration and processing 24 of FIG. 21 is another component in the Cloud-based server 122. Calibration and processing 24 is responsible for removing system error and acquisition setting deviation due to any environment inconsistency from uploaded acquisition data (two curves). In order to have a hyperspectral model to analyze, match acquisition data and provide test results independent from instruments and acquisition environments, each instrument 10 may carry characteristic curves (for entire 600 nm bandwidth). The characteristic curve for each device should be measured by a standard optical plate in an environment based on the peripherals accompanying the instrument prior to release to user. Periodically, users of the instrument should conduct a similar process with the same setting (not necessarily exactly conditions) to obtain calibration curves. The difference between the characteristics curve and the calibration curve for each instrument is used to calculate a compensation curve to apply to each acquisition data point to correct the deviation introduced by instrument and acquisition environment, as well as that caused by worn out and inconsistent operation.

Preferably, calibration is conducted periodically by user applying the necessary calibration procedures to generate calibration curves according to the application. However, the role of calculating compensation curves and applying correction to acquisition data is that of the calibration and processing component in the Cloud-based server 122.

Hyperspectral Model Matching is another component of the system 11 which is part of the Cloud-based server 122. This component takes acquisition data from a lubricant oil sample as input, after calibration of the two curves, then outputs quantitative analysis elements for the lubricant oil sample, such as iron (Fe) and copper (Cu) content (in mg/L). The hyperspectral model matching component consists of a Hyperspectral Library in which a collection of element spectrum is placed, such as spectral extraction, spectral discrimination, and spectrum matching processing components.

The Hyperspectral Model Matching has two tasks. The first task, based on a limited number of laboratory oil sample test results, which statistically cover entire subject lubricant application lifecycle distribution and acquisition data of these oil samples, is to build a Hyperspectral Model. The second task, based on the Hyperspectral Model, is to calculate the element from input acquisition data (two curves) in a lubricant oil sample within its distribution. This is described in further detail below.

Figure 24:
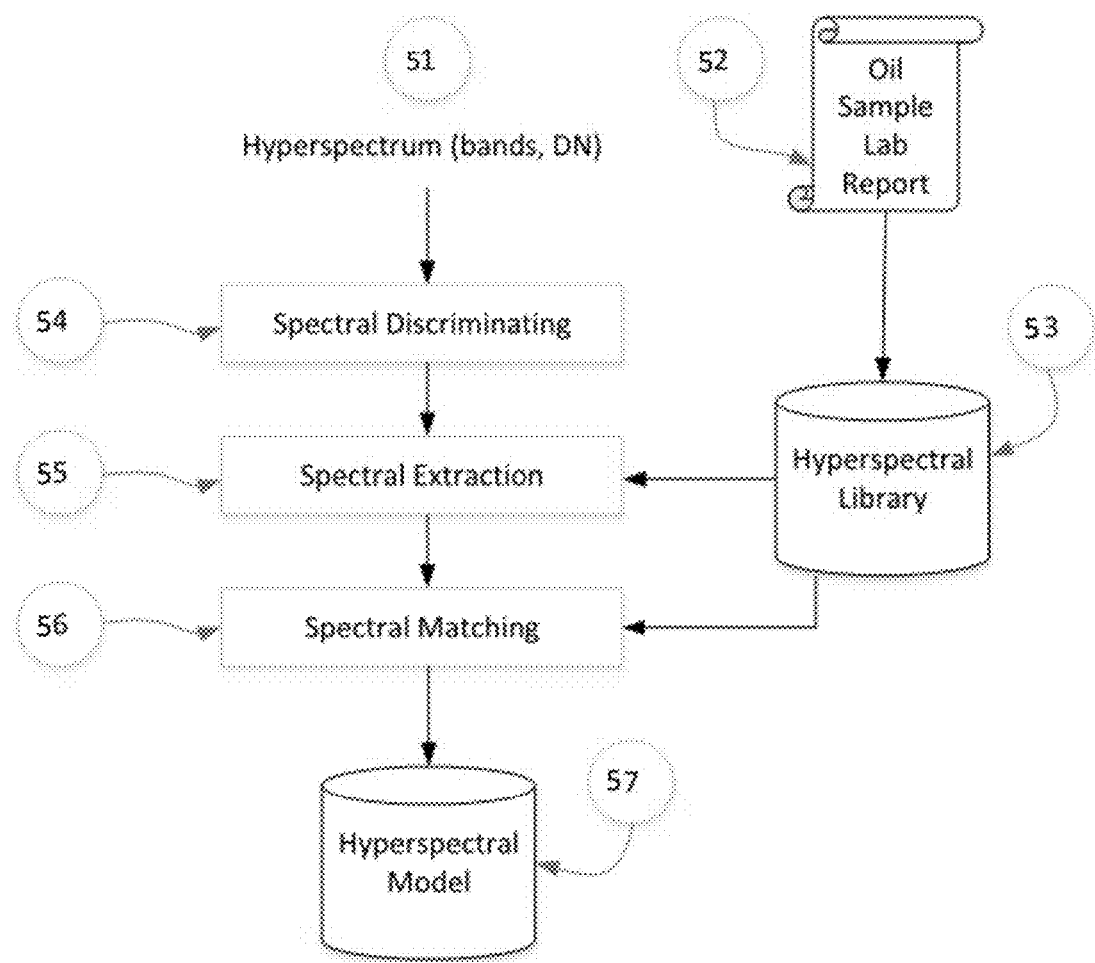
FIG. 24 is the Processing Procedures to Calculate the Test Results.

In order for the system to quantitatively measure elemental contents in the lubricant oil sample, it needs to build Hyperspectral Model based on the same type of subject lubricant oil. Such a process is described in detail above. FIG. 24 is a flowchart illustrating more generally, how to build a proper Hyperspectral Model. The process requires a certain number of oil samples distributed throughout the entire lifecycle of the specific lubricant.

To briefly summarize the detailed process provided above in the present disclosure, a preferred embodiment of the process for building a hyperspectral model is as follows:

1. Obtain laboratory test results of a given number of oil samples;
2. Use disclosed system to acquire data points for oil sample to plot its two curves (see FIG. 24, ref. No. 51).
3. Input laboratory test report of the same oil sample into the system (see FIG. 24, ref. No. 52);
4. The laboratory result of the oil sample determines which elements and other contents the system will measure (see FIG. 24, ref. No. 53);
5. For all elements, two curves represent reflection and DN values for entire bandwidth of 400-1000 nm, or approximately 200-300 intervals/data points. In order to discriminate, identify, or detect target of interest, a spectral derivative feature coding is applied to hyperspectral signature discrimination and data classification (see FIG. 24, ref. No. 54);
6. For specific elements, only reflection and DN values of subset intervals are needed. The computational intelligence method for band selection, as known by those in the art, combined with the specific element-defined parameters from the Hyperspectral Library after inputting laboratory results of oil samples, will yield better extraction results (see FIG. 24, ref. No. 55);
7. The element corresponding to bands from Hyperspectral Library is used to match reflection and DN values of bands. The quantitative content of the element from the laboratory results is paired to the characteristic of reflection and DN values (see FIG. 24, ref. No. 56);
8. The paired result corresponding to the laboratory test element content, reflection and DN values of the bands, are stored, which represent the element content of the oil sample in the Hyperspectral Model (see FIG. 24, ref. No. 57);
9. The process of steps 6-8 is repeated until all elements in the laboratory test result in the oil sample are counted; and
10. The process is then repeated, beginning with step 2 above, until all oil samples used to build Hyperspectral Model are counted.

The Hyperspectral Model 57 indicates the relationship between each element content corresponding to reflection and DN values of bands for a type of lubricant. Experimental results suggest that Hyperspectral Model 57 can hold multiple types of lubricants independent from the engine or rotating equipment to which it is applied.

It is easy to understand that a Hyperspectral Model 57 binds a type of lubricant or an application scenario. The Hyperspectral Model 57 can be assigned ID which can be associated with the lubricant oil sample container ID. In another words, the instrument obtains the lubricant oil sample container ID through near field communication (NFC) protocol, the system is able to pair the Hyperspectral Model to measure its acquisition data (two curves).

Figure 22:
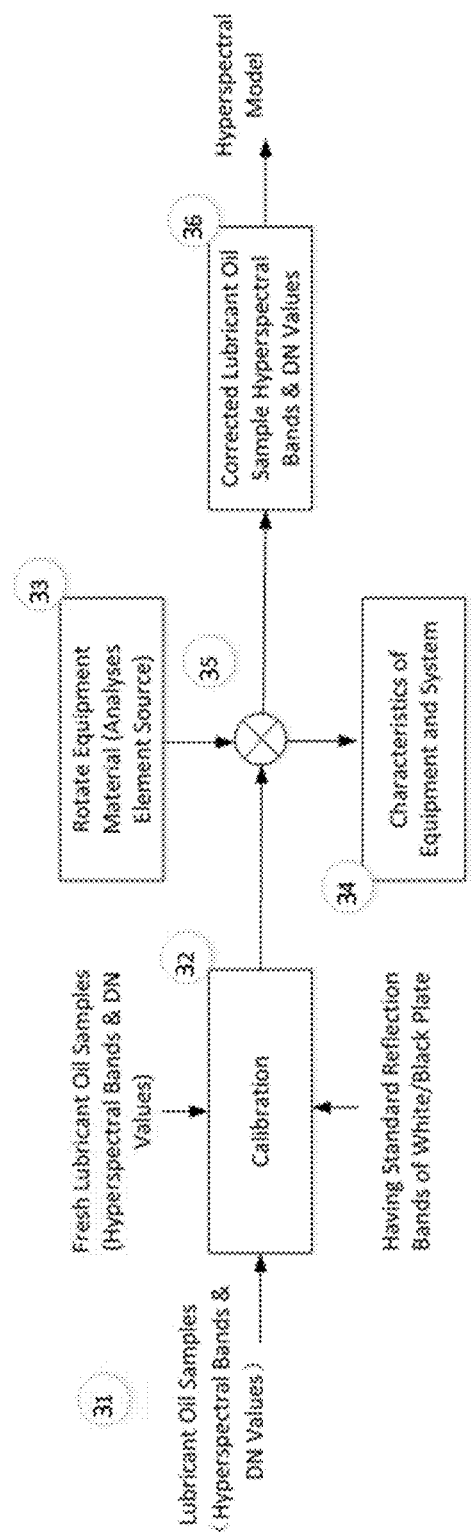
FIG. 22 is a system diagram of an embodiment of system calibration and an application-driven expert system.

FIG. 22 is the system diagram of Calibration and Expert System. It includes two procedures. One is for calibration (see FIG. 22, ref. No. 32) and the other is for an application driven expert system (see FIG. 22, ref. Nos. 33, 34 and 36). Both make sure to provide quality and better resolution acquisition data (two curves) for the Hyperspectral Model matching processing.

Acquisition inputs include dedicated data for calibration. For example, fresh lubricant oil sample reflection and DN values (i.e., clean oil before use) based on bands, and standard black and white optical plate reflection and DN values can be used as baselines (see FIG. 22, ref. No. 32). That is, the fresh lubricant oil sample reflection and DN values can actually provide a way to remove background noise from normal acquisition data (i.e., reflection and DN values) through a subtraction corresponding to each band. This calibration enhances metal dust elements introduced in actual oil samples during the normal operation of lubricating engines or rotary equipment. Likewise, the standard black and white optical plates produce known reflection and DN values during initialization.

The same procedure can be used to measure plates at "power on" for the instrument prior to each testing. Any differences recorded over time will reflect degradation of the instrument. However, the system can use the measured difference to calculate a compensation value for the reflection and DN values of the acquisition data in real time. Accordingly, calibration is a processing unit of the system to measure and calculate the compensation needed to obtain correct and consistent reflection and DN values for each band.

Understanding measurement equipment and determining the elements in an oil sample to measure will help the Hyperspectral Model matching procedure. For example, it can help in the diagnosing of the subject engine or equipment runtime condition by knowing characteristics of the engine, equipment, or system (see FIG. 22, ref. No. 34). It also helps the system to interpolate the acquisition data. Using the disclosed process will present acquisition data, include reflection and DN values, after the necessary correction is applied. As a result, it will minimize the dependence of the acquisition data on different instruments, environment, and the operator.

Figure 23:
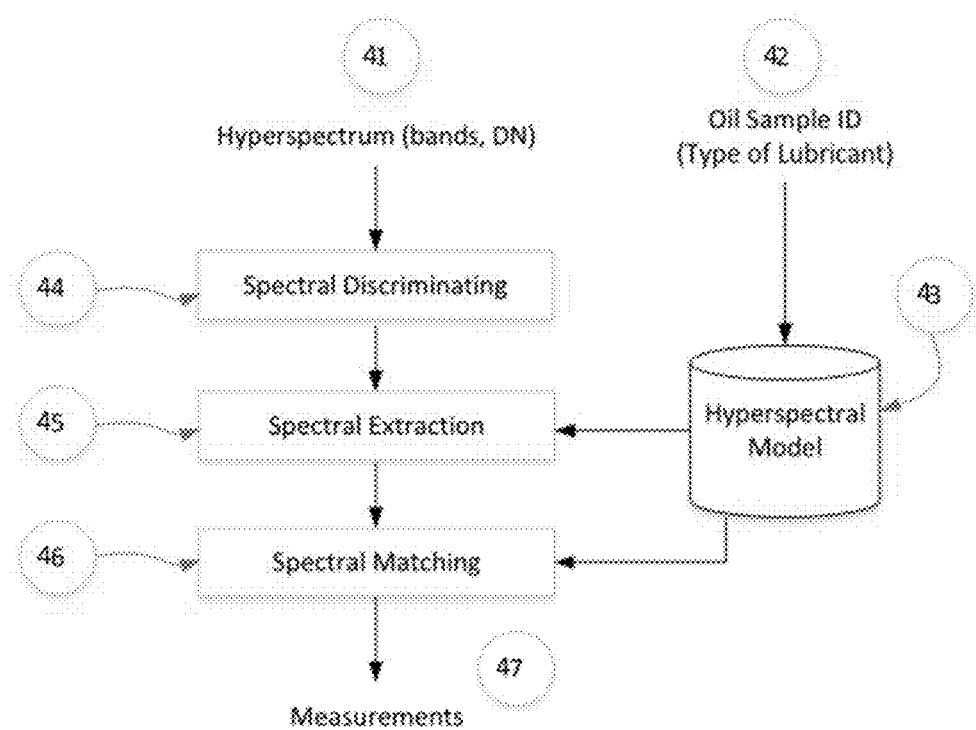
FIG. 23 is a flow chart illustrating a processing procedure for building hyperspectral models.

FIG. 23 is a flowchart illustrating how to measure the element content from the acquisition data acquired from a lubricant oil sample in the field. The flowchart is explained in more detail below:

1. The instrument 11 is used to read the oil sample container ID and acquires the oil sample to get its two curves (see FIG. 23, ref. No. 41);
2. The system matches the Hyperspectral Model with the oil sample container ID (see FIG. 23, ref. No. 42);
3. For all elements, two curves represent reflection and DN value of entire bandwidth of 400-1000 nm, ranging between 200-300 intervals/data points. In order to discriminate, identify, or detect target of interest, a spectral derivative feature coding is applied to hyperspectral signature discrimination and data classification (see FIG. 23, ref. No. 44);
4. For a specific element, the system only needs reflection and DN values of a subset of intervals. As previously noted, the computational intelligence method for band selection combined with element-defined parameters from Hyperspectral Model 68 will yield better extraction results (see FIG. 23, ref. No. 45);
5. The element corresponding to bands from the Hyperspectral Model 43 are then used to match reflection and DN values of bands, locate "neighbors" of reflection and DN values of bands, apply bandwidth spatial convolution to interpolate quantitative content of the subject element from the Hyperspectral Model (see FIG. 23, ref. No. 46);
6. The measured element content of the oil sample is then stored in a system database with an index of the oil sample container ID (see FIG. 23, ref. No. 47). The stored data may be used to associate a point in test or engine service records with a time label; and
7. The process is repeated from step 3 above until all elements in the oil sample are counted.

With the procedures disclosed above, comparable laboratory test results of a lubricant oil sample can be obtained using the disclosed hyperspectral sensing instrument 10 and system, in as little as a few seconds. The instrument 11 is lightweight, preferably handheld, compact enough to fit any specific application scenario, and easy enough to operate by maintenance personnel that it does not require a dedicated technician.

The instrument 11 provides at least two opportunities for better maintenance and service, including 1) providing a direct diagnosis of the "health status" of equipment as a clinic physical exam report rather than merely providing element contents in the oil sample that would require dedicated personnel to interpret, and 2) keeping the instrument independent from the specific application scenario and the Hyperspectral Model independent from the instrument, which allows the Hyperspectral Model to leverage big data self-learning and improve the precision and sample interval of the lubricant. An Application Driven Expert System (see FIG. 21, ref. No. 26) in the Cloud-based server is designed to satisfy these two opportunities and more.

The Application Driven Expert (ADE) System is a self-sufficient container (i.e., as in software terminology, not a physical container), automatically deployed by the system based on an application that can run in the Cloud-based server. The ADE System offers an end user access to the system. It corresponds to at least one instrument by binding its ID. It provides an application scenario to input the way a skilled technician and/or scientist using test results of an oil sample to diagnosis or analysis the "health condition" of a machine, wind turbine, vehicle, ship, or a jet engine, etc., and to make a recommendation based on the analysis. For example, a certain level of iron (Fe) content in a lubricant oil sample from a wind turbine would mean the wind turbine paddle bearings are worn out. As a result, a maintenance procedure may be recommended. Such a threshold level can be set into the "container" to trigger an alert. Since the instrument 10 binds to the application (via ID), it can be operated by a less skilled worker on site to obtain the same diagnosis and recommendation in seconds.

FIG. 24 is the Processing Procedures to Calculate the Test Results. It includes the following steps:

1. Obtain oil sample container ID from the instrument to determine the corresponding Hyperspectral Model to use (through UID).
2. Use the instrument to acquire the reflection and DN values with entire bandwidth from the oil sample as input.
3. Hyperspectral Model is the data base unit in which the spectrum including reflection and DN values of element contents corresponding to reflection and DN values of entire bandwidth obtained from a set of oil sample from a type of lubricant are stored.
4. It is a standard data processing utilities to enhance acquisition data (step 2 above).
5. It is a standard data processing utilities to extract a subset of bands for specific element to be measured according to Hyperspectral Model reference.
6. It is the procedure to use Hyperspectral Model contents according to the matching mechanism to interpolate the characteristics of the reflection and DN values of input oil samples.
7. The corresponding results (element content) are stored in the data base indexed by the oil sample (container) ID with oil sample acquisition time label attached.

Figure 25:
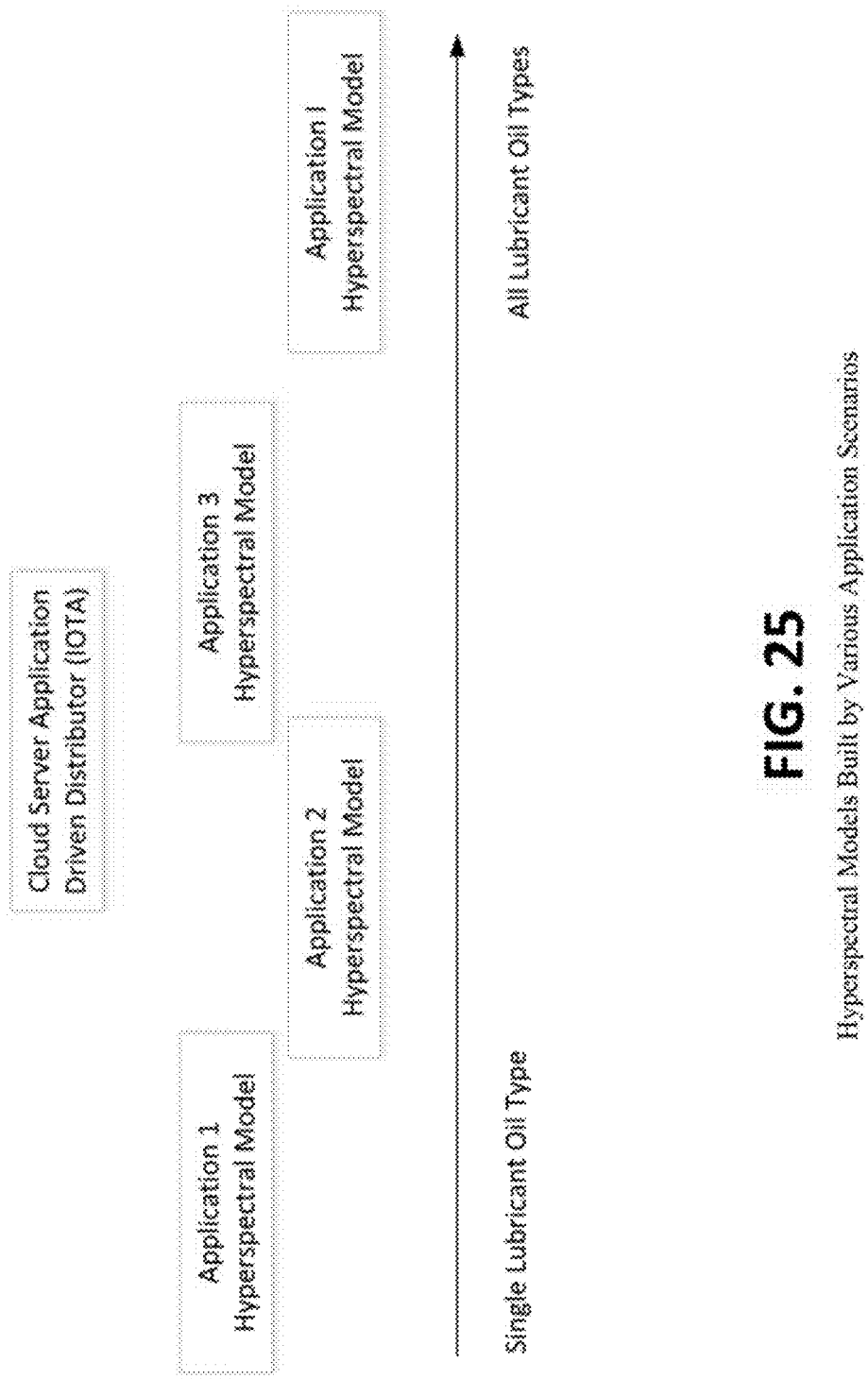
FIG. 25 illustrates a number of hyperspectral models built by various application scenarios in the system.

FIG. 25 illustrates a number of hyperspectral models built by various application scenarios in the system. When the same type of lubricant oil is taken from the same or different engine or equipment scenarios, the system is able to reconstruct the existing hyperspectral model for that lubricant oil to create a new one with better precision without user interruption for a specific scenario. This is referred to as "self-learning" and greatly improves precision of the instrument.

Based on various applications, the system can deploy appropriate self-sufficient containers. Each software container corresponds to an application scenario, while each application corresponds to a Hyperspectral Model. The more application scenarios deployed, the greater the number of Hyperspectral Models in the system to be built (see FIG. 25).

In a situation where there are different applications for the same type of lubricant, then multiple Hyperspectral Models create overlap in data and provide more detection area for the lubricant. The greater data allows the system to update/reconstruct the Hyperspectral Models, whereby precision becomes much better for the overlapping area, and the detection range may even increase.

For example, using a wind turbine analysis for iron (Fe) content, two Hyperspectral Models (e.g., different customers) might correspond to 2 megawatt (MW) and 4 MW wind turbine applications. Both turbines use the same lubricant in the paddle bearing. Iron (Fe) content ranges between 0-1300 mg/kg in the Hyperspectral Model of the 2 MW wind turbine, while the Fe content range is between 300-1800 mg/kg in the Hyperspectral Model of the 4 MW turbine. With data from both models, the Hyperspectral Models of both the 2 MW and 4 MW wind turbines can be reconstructed/updated by the system. This process increases precision as a result of the increase in sample size. It also expands the analysis range for the wind turbines when the iron (Fe) content increases beyond the original modeling area. Iron, as well as other materials, can be quantitatively measured and exceeding thresholds can trigger an alert when anything potentially catastrophic happens in the bearings. As a result, the instrument improves its measure area and precision by self-learning.

The system includes a database which stores data, including the measure results, diagnosis, and any recommendations according to the acquisition time stamp. It is herein referred to as the "Measure Result & Diagnosis" component in the Cloud-based server 122 (see FIG. 2). This component is the foundation of the sample analysis methods, trends of Lubricant changes by run time, data display corresponding to bands, time, application mark, and recommendations. The results, including data display, can be pushed to the remote instrument on site through the Information Platform (see FIG. 2, ref. No. 23).

The beneficial effects of the present invention are numerous. For example, the method is suitable for obtaining detection results for metal components, particle size, viscosity, and chemical components simultaneously in a single operation. This simplifies operation, economizes consumables, and achieves the effect of portable real-time detection, thereby eliminating the need for specialized operators involved.

As used herein, the word "preferred" means serving as an example, instance, or illustration. Any aspect or design described herein as "preferred" is not necessarily to be construed as advantageous over other aspects or designs. Rather, the use of the word "preferred" is intended to present concepts in a specific manner. The term "or" as used in this application is intended to mean an inclusive "or" rather than an exclusive "or." That is, unless it is specified otherwise or is clear from context, "X employs A or B" is meant to naturally include either one of the permutations. That is, "X uses A or B" is satisfied in any of the following examples: X uses A; X uses B; or X uses both A and B.

Although the present disclosure has been revealed and described with respect to one implementation mode, equivalent variations and modifications will occur to those skilled in the art based on a reading and understanding of this description and the drawings. The present disclosure includes all such variations and modifications and is limited only by the scope of the appended claims. In particular, with respect to the various functions performed by the components set forth above (such as elements), the terms used to describe such components are intended to correspond to any component that performs the specified function of the component (that is, which is functionally equivalent) (unless otherwise indicated), even if not structurally equivalent to the disclosed structures that perform the functions of the exemplary implementation modes of the present disclosure shown herein.

Furthermore, although particular characteristics of the present disclosure have been disclosed with respect to only one of several implementation modes, such characteristics may be combined with one or other characteristics of other implementation modes as may be desirable and advantageous for a given or particular application combination. Moreover, to the extent that the terms "including," "having," "containing," or variations thereof are used in the detailed description or the claims, such terms are intended to include in a manner similar to the term "comprising."

Each functional unit in the embodiment of the present invention may be integrated into a single processing module, or each unit may exist physically alone, or several or more units may be integrated into one module. The above integrated modules may be implemented in the form of hardware or may be implemented in the form of functional software modules. If the integrated modules are implemented in the form of functional software modules and sold or used as independent products, they may also be stored in a computer-readable storage medium. The above storage medium may be a read-only memory, a magnetic disk, an optical disc, and the like. The above devices or systems may execute the storage methods in corresponding method embodiments.

In sum, the above embodiment is an implementation mode of the present invention, but implementation modes of the present invention are not limited by the embodiment. Any other changes, modifications, substitutions, combinations, and simplifications that do not deviate from the spirit or principle of the present invention should all be construed as equivalent substitutions that are contained within the protective scope of the present invention.

The matter set forth in the foregoing description and accompanying drawings is offered by way of illustration only and not as a limitation. While particular embodiments have been shown and described, it will be apparent to those skilled in the art that changes and modifications may be made without departing from the broader aspects of applicants' contribution. The actual scope of the protection sought is intended to be defined in the following claims when viewed in their proper perspective based on the prior art.

What is claimed is:

1. An analysis device for determining element concentration in a lubricant oil based on reflected hyper-spectral spectrum, the device comprising:
  a housing having positioned therein:
    a halogen light source;
    a probe grating splitter;
    a light transmission lens bracket and a convex lens;
    an optical system including a detector; and
    a dark chamber configured for insertion of a colorimetric dish, the dark chamber comprising an aperture, a spring, a standard light plate, a rotating shaft seat, a rotating shaft seat cover, a rotating shaft, and a lower cover;
  wherein,
    the lower cover is sequentially provided with a convex lens slot, a colorimetric dish hole and a standard optical plate slot, each arranged in parallel;
    the convex lens is configured to be inserted into the convex lens slot, and the standard optical plate is configured to be inserted into the standard optical plate slot;
    the dish hole is used for holding the colorimetric dish;
    an end of the spring is connected with the rotating shaft seat, and another end of the spring is connected with the rotating shaft;
    the rotating shaft is positioned to fix the colorimetric dish;

the rotating shaft is symmetrically arranged along the colorimetric dish hole, with one end inserted into the rotating shaft seat, and another end pressing against the colorimetric dish;

the rotating shaft seat is positioned and set to permit the rotating shaft to move in a single direction when the colorimetric dish is inserted into the colorimetric dish hole to thereby exert pressure on the rotating shaft; and the spring pulls the rotating shaft so as to press on the colorimetric dish to make it fixed.

2. The analysis device for determining element concentration in a lubricant oil as set forth in claim 1, further comprising a server electronically coupled to the optical system and configured to preferentially determine a reflectance rate and a DN value of the standard module plate and the standard optical plate to compare with a reflectance rate and a DN value of a benchmark machine.

3. A single operation detection method for detecting multi-type metrics of oil samples, comprising the steps of:
   establishing a relationship between a plurality of oil sampling points and test results, wherein:
      the plurality of oil sampling points comprise changes in oil sample component contents at a time of sampling over a sampling period; and
      the test results comprise algorithm models to which a hyperspectral oil detection device corresponds;
   building a model library comprised of oil sample information related to oil performance, brand, grade, operating equipment, detection components, and sampling points;
   storing the model library onto a server;
   obtaining an oil sample to be analyzed;
   transferring the oil sample into a cuvette of a hyperspectral oil detection device having an optical system;
   assigning the oil sample an identification number;
   using an optical system of the hyperspectral oil detection device to generate reflectance and radiance values (DN value) for the oil sample; and
   bundling the reflectance and radiance values with a sampling point for the oil sample;
   uploading the bundled values and sampling point to the server together with the oil sample identification number and a detection time;
   selecting a model algorithm based on the sampling point of the oil sample;
   selecting one or more secondary model algorithms based on settings to determine the reflectance and DN values obtained in a collection operation; and
   activating multiple threads based on different model algorithms while also pushing the reflectance and DN values of the oil sample being tested to each thread for simultaneous model calculation.

4. The single operation detection method according to claim 3, further comprising the step of performing adaptive learning based on a base oil sample before a model is selected for a first time for analysis.

5. The single operation detection method according to claim 4, wherein the step of performing adaptive learning comprises a folded subset interleaved prediction response method and partial least squares modeling prediction.

6. The single operation detection method according to claim 5, wherein using partial least square modeling prediction, some subsets are used for observation, and the number of subsets being related to a distribution gradient of the oil sample group being modeled, and with the resulting response being evaluated by mean square deviation.

7. The single operation detection method according to claim 3, further comprising the steps of dividing sample data into a training set and a test set based on a modeling dilution gradient distribution or a dependent variable, wherein only the data in the training set are used to train and refine the model, then the model is used to make predictions for the test set, and the response test mean square error is calculated;

repeating the previous steps K times, where K is the number of dilution gradient distribution intervals, with a different training set and test set being used each time, with the model making the predicted value approach the output of the model training set based on the number of training iterations; and adopting the mean of the K test mean square errors as the overall test mean square error (MSE).

8. The single operation detection method according to claim 7, further comprising the steps of:
   diluting the actual oil samples having laboratory detection results based on the concentration gradient with the base oil by the volume specific gravity method to obtain a group of oil samples of known distribution;
   generating from the oil sample group a set of DN values and reflectance values with a hyperspectral oil detection device, wherein each set of DN values corresponds to a set of reflectance values based on spectra;
   inputting the reflectance and DN value series into the model one by one;
   employing partial least squares method to analyze the statistical relationship between a dependent variable and an independent variable, with the dependent variable Y being a metal component of the oil sample at a certain dilution distribution point at the sampling point;
   calculating the test index and the concentration of the dilution distribution point index to conduct calibration, and these are iteratively converged on a specified MSE range; and
   repeating the above steps i times, with $1<i<K$, with K beginning at 0, a different training set and test set are employed each time, representing different gradients of the oil sample dilution distribution, with the model causing the predicted value to approach the output of the model training set based on the number of training iterations.

9. The single operation detection method according claim 4, wherein the partial least squares method comprises the steps of:
   establishing a remaining information matrix $E_0$ and a detection oil sample component matrix $F_0$, where $E_0$ is a standardized independent variable matrix, each row is a series of component indexes, and each column denotes a set of spectral band variables corresponding to the detection element indexes; $F_0$ is a dependent variable matrix; similarly to $E_0$, each row is a series of component indexes, and each column denotes a set of spectral band variables corresponding to the detection element indexes; where data normalization consists of subtracting the mean of each spectral band, and then dividing by the standard deviation of each spectral band;
   solving for the eigenvector $w_1$ corresponding to the maximum eigenvalue of the matrix $E_0^T F_0 F_0^T E_0$ to obtain a component score vector $\hat{t}_1 = E_0 w_1$ and a remaining information matrix $E_1 = E_0 - \hat{t}_1 a_1^T$, wherein $a_1 = E_0^T \hat{t}_1 / \|\hat{t}_1\|^2$;
   solving for the eigenvector $w_2$ corresponding to the maximum eigenvalue of the matrix $E_0^T F_0 F_0^T E_1$ to obtain a component score vector $\hat{t}_2 = E_0 w_2$ and a residual information matrix $E_2 = E_1 - \hat{t}_2 a_2^T$, wherein $a_2 = E_1^T \hat{t}_2 / \|\hat{t}_2\|^2$;

repeating the above steps to the $m^{th}$ step, solving for the eigenvector $W_m$ corresponding to the maximum eigenvalue of the matrix $E_{m-1}^T F_0 F_0^T E_{m-1}$ to obtain a component score vector $\hat{t}_m = E_{m-1} w_m$;

based on cross validity, determining that a total of m components $t_1, t_2, \ldots, t_m$ have been extracted to obtain a satisfactory predictive model; solving the common least squares regression equation for $F_0$ on $t_1, t_2, \ldots, t_m$:

$$F_0 = \hat{t}_1 \beta_1^T + \hat{t}_2 \beta_2^T + \ldots + \hat{t}_m \beta_m^T + F_m$$

wherein $\beta_1$, $\beta_2$, and $\beta_m$ denote the weighting parameters of the $1^{st}$, $2^{nd}$, and $m^{th}$ components, respectively, and Fm denotes the remaining information matrix after extracting m components;

if data tables X and Y are subjected to m components being extracted for X, substituting $t_k = w_{k1}^* x_1 + w_{k2}^* x_2 + \ldots + w_{kn}^* x_n$, (k=1, 2, \ldots, m) into $Y = t_1 \beta_1 + t_2 \beta_2 + \ldots + t_m \beta_m$ to obtain a partial least squares method regression equation of p dependent variables:

$$y_j = a_{j1} x_1 + a_{j2} x_2 + \ldots + a_{jn} x_n (j=1,2, \ldots, p)$$

such that $w_h^* = (w_{h1}^*, w_{h2}^*, \ldots, w_{hn}^*)^T$ satisfies $\hat{t}_h = E_0 w_h^*$ and $$w_h^* = \Pi_{j=1}^{h-1}(I - w_j a_j^T) w_h$$

wherein I is the label parameter of a detected index corresponding to a dependent variable j, h is the dimension of Y, that is, the number of spectral segments, $a_{jn}$ is a model matrix parameter, where j denotes a component index, n denotes a spectral band index, and $w^*_{kn}$ is the remaining information eigenvector of the $k^{th}$ detection component index relative to the $n^{th}$ spectral band.

10. The single operation detection method according to claim 8, wherein the volume specific gravity method comprises the steps of:

injecting 10 mL of the oil sample into a test tube;

calculating the unit specific gravity of the oil sample based on the weight difference, and obtaining the unit specific gravity of the base oil and of the oil sample with laboratory test results;

obtaining the weight of the test oil sample and the base oil that require dilution in the cuvette;

calculating the weights of two oil samples introduced into a 3.4 mL cuvette and mixed based on the weights of two different 10 mL oil samples;

based on the dilution point, calculating the weight of the base oil and the weight of the test oil sample to be separately charged to the cuvette by the following calculation method:

$$x_{oil\,sample\,tested} = \frac{W_{cuvette} * \text{target dilution concentration}}{\text{component being detected}}$$

wherein $x_{oil\,sample\,tested}$ is the weight of the oil sample being tested to be introduced based on the target dilution concentration, $W_{cuvette}$ is the weight of the oil sample to be charged to the cuvette, the target dilution concentration is the dilution point of the oil sample being tested relative to the accompanying laboratory test results, and the component being detected is the target component in the oil sample being tested of the accompanying laboratory test results;

the weight of the base oil to be added to the cuvette is:

$$W_{cuvette} - x_{oil\,sample\,tested}$$

using an electronic balance, the cuvette is placed in a holder, which is then placed on the balance to obtain the net weight; and introducing the test oil sample and the base oil into the cuvette based on the weights that have been calculated to reconstruct a test oil sample at the dilution point.

11. A consistency measurement calibrator for a hyperspectral lubricant oil detection device, characterized in that an overall consistency required for the device includes cumulative consistency of a light source, a grating separation, and a photoelectric conversion circuit, and the overall consistency is reflected by changes in reflectance rate and DN value, wherein the consistency measurement calibrator comprises:

a dark chamber of a cuvette, a halogen light source, a probe grating splitter, a light transmission lens bracket and a convex lens;

the dark chamber of the cuvette comprises a cuvette hole, a spring, a cuvette, a standard light plate, a rotating shaft seat, a rotating shaft seat cover, a rotating shaft, and a lower cover;

wherein, the lower cover is sequentially provided with a convex lens slot, a cuvette hole and a standard optical plate slot arranged in parallel;

the convex lens can be inserted into the convex lens slot, and the standard optical plate can be inserted into the standard optical plate slot;

the cuvette hole is used for holding the cuvette;

an end of the spring is connected with the rotating shaft seat, and another end of the spring is connected with the rotating shaft;

the rotating shaft is made of an elastic material, which is used to fix the cuvette; the rotating shaft is symmetrically arranged along the cuvette hole, with one of its ends inserted into the rotating shaft seat, and the other end pressing against the cuvette; the rotating shaft seat is set to ensure that the rotating shaft shall move in only one direction after being subjected to a force; when the cuvette is inserted into the cuvette hole, the pressure exerted on the rotating shaft by the cuvette pushes the rotating shaft to rotate horizontally; and with the cuvette thoroughly inserted to the bottom, the spring pulls the rotating shaft so as to press on the cuvette to make it fixed to prevent it from shaking and moving in the cuvette hole.

12. The consistency measurement calibrator according to claim 11, wherein a distance and parallelism between the light-transmitting surface of the cuvette and the convex lens are guaranteed by the two rotating shafts via the spring and the rotating shaft seat, which are used to fix the cuvette.

13. The consistency measurement calibrator according to claim 12, wherein the rotating shaft is subjected to a force causing it to move in the opposite direction to a transparent surface of the cuvette, and such movement causes tension in the spring as the matching fixing part, which in turn causes the cylindrical rod to produce a reaction force that presses on the transparent surface of the cuvette for stabilizing.

14. The consistency measurement calibrator according to claim 12, wherein the halogen light source and the probe grating splitter are fixed by the structural component of the dark chamber to determine the angle of the projection light path and the reflectance angle, and which are arranged in front of the dark chamber of the cuvette.

15. A consistency measurement calibration method for a hyperspectral lubricant oil detection device according to claim 12, the calibration method comprising the steps:
- conducting measurement through the standard module optical plate;
- obtaining reflectance rate and the DN value;
- recording any deviation of the obtained reflectance rate and DN value between the detection device and a benchmark machine; and
- calibrating the detection device if a deviation is recorded.

16. The consistency measurement calibration method for a hyperspectral lubricant oil detection device according to claim 15, further comprising testing for consistency comprising the steps of:
- establishing a device as a benchmark machine;
- positioning a standard module light plate of the same size as the cuvette into the cuvette hole with the surface of the standard light plate of the standard module light plate facing the direction of a see-through lens;
- obtaining initial reflectance rate and DN value of the benchmark machine;
- storing the initial reflectance rate and DN value of the benchmark machine in the spectral model server;
- testing a second device, different than the benchmark machine, using a standard module optical plate;
- recording a reflectance rate and DN value for the second device;
- storing the reflectance rate and DN value of the second device in the spectral model server;
- comparing the reflectance rate and the DN value of the standard module plate of the second device with the reflectance rate and the DN value of the modeling benchmark machine to obtain measurement errors; and
- correcting the reflectance rate and the DN value so that the test results of the benchmark machine and those of the second device are consistent.

17. The consistency measurement calibration method for a hyperspectral lubricant oil detection device according to claim 16, wherein the testing for consistency further comprises the step of maintaining the parallel position and the distance between the cuvette and the light-transmitting lens are kept consistent for each insertion of the cuvette, each closure of the cover of the cuvette's dark chamber, and each initiation of detection.

18. The consistency measurement calibration method for a hyperspectral lubricant oil detection device according to claim 17, wherein error caused by the transparent surface before and after the cuvette is expressed as:

Error(x)=Opt(x)−f(x)

wherein x represents a detected component; f (x) represents test result of a certain transparent surface of the cuvette; Opt (x) represents test result of a one-time random operation of insertion; Error (x) represents error introduced by a pure operation that excludes errors of the transparent surface of the cuvette itself, and f (x) is calculated as:

$$f(x) = \text{Max}\left(\frac{1}{N}\sum_{n=1}^{N} \text{(Two cuvette transparent surfaces of } A \text{ and } B \text{ are continuously tested respectively)}\right),$$

wherein N represents the number of times of continuous measurements, A represents any transparent surface of the cuvette, and B represents another transparent surface of the cuvette directly across from A; and wherein Opt (x) is calculated as:

$$Opt(x) = \text{Max}\left(\frac{1}{N}\sum_{n=1}^{N} \text{(The actual operation of testing with a cuvette)}\right)$$

wherein N represents the number of times of continuous measurements, and "the actual operation of testing with a cuvette" means the whole process of random inserting, testing, and removal of the cuvette.

19. A lubricant oil analysis method based on reflected hyper-spectrum, the method comprising the steps of:
- (S1) modeling standard oil samples with identical concentration distributions of multiple indices by:
  - selecting a plurality of standard oil samples;
  - obtaining through dilution and calibration operations a distributed standard oil group covering a preset spectral band, with a component distribution of the distributed standard oil group corresponding to different spectra;
  - establishing multiple hyperspectral spectral bands for the distributed standard oil group and a spectral model for a single known standard oil component index, with the spectral model being a parameter matrix; and
  - testing the spectral model, wherein the hyperspectral spectral band detected for the distributed standard oil group is adopted as an independent variable, a parameter matrix is incorporated, and partial least square method is used to achieve convergence and obtain a dependent variable, with the dependent variable being the standard oil component index of the distributed standard oil group;
- (S2) specifying indices and modeling standard oils with different concentration distributions, comprising the steps of:
  - selecting a standard oil;
  - based on a known concentration and composition of the standard oil, using dilution and calibration operations to repeat the (S1) modeling step;
  - establishing a spectral model covering a distributed standard oil group;
  - establishing a standard test template based on the dilution method and the covered distribution; and
  - establishing and testing primary hyperspectral and spectral models of multiple known standard oil component indices of the standard test template;
- (S3) modeling standard oil with different concentration distributions of different indices, comprising the steps of:
  - selecting a single component distributed standard oil group;
  - adding specified indices and concentrations of actual oil sample distributions in an application scenario;
  - repeating step S2 through the dilution and calibration operations to establish a distributed standard oil group covering the application scenario; and
  - based on the distributed standard oil group covering the application scenario, establishing and testing a secondary hyperspectral model and multiple spectral models of known standard oil component indices;
- (S4) sampling the test results and comparing the same to atomic emission spectrometer detection results of corresponding oil samples;

adjusting the detection results by nonlinear data fitting;
adjusting the calculated deviation of the secondary spectral models based on the nonlinear data fitting, so that the detection results are fitted to the atomic emission spectrometer detection results;

(S5) modeling a target detection oil brand and the manufacturer's base oil combined with a specified index standard oil, comprising the steps of:
  selecting a standard oil and a base oil in actual use;
  repeating S3 steps with the selected standard oil and base oil in actual use;
  using the dilution method to establish a distributed standard oil group covering a predetermined application scenario;
  causing the specified index of the distributed standard oil group to conform to the actual oil sample distribution in the application scenario;
  establishing and testing a spectral model based on the distributed standard oil group;
  customizing the standard oil;
  mixing the customized standard oil with an oil sample to be tested;
  establishing a standard oil group with an actual oil sample distribution covering the application scenario to which particle size interference has been added;
  establishing and testing a spectral model based on the distribution of the standard oil group;
  evaluating interference of particle size on the spectral model and a corresponding anti-interference scheme;
  combining the spectral model with application scenario detection components;
  establishing a series of spectral models for different base oils and standard oils of specified indices; and
  establishing and storing a spectral model library based on the base oils of different manufacturers and brands in conjunction with application scenarios;

(S6) based on the stored spectral model library, comparing oil samples with the same base oil in laboratory test results to achieve learning improvement; and (S7) modeling actual oil samples, comprising the steps of:
  using the base oil of an oil sample and an oil sample having the most concentrated components collected during an actual oil change, and repeating step S6, using the dilution method to establish a distributed oil sample group, which will cause the distributed oil sample group to conform to the actual oil sample distribution in the application scenario;
  establishing and testing a spectral matrix model, and if there is a difference in accuracy, employing step S6 to improve the accuracy.

20. The lubricant oil analysis method according to claim 19, wherein the testing comprises:
  employing a 400 nm to 1,000 nm halogen light source, loading the oil sample to be tested in a cuvette transmitting light through both sides, inserting the cuvette into a dark chamber, and obtaining a spectrum of specific wavelength over a reflected light path; and
  utilizing the ideal state of the standard oil, establishing a spectral model based on the oil sample being tested and the content distribution of detected components, performing calculations for the oil sample being tested based on a statistical and inferred regression algorithm, using a likelihood estimation function rapid convergence model, and achieving device accuracy under ideal conditions.

21. The lubricant oil analysis method according to claim 19, wherein the spectral model has a relationship such that a spectral band n is taken as an independent variable $\{x_1, \ldots, x_p\}$ to calculate the detection index p as a dependent variable $\{y_1, \ldots, y_n\}$, and based on the statistical relationship between the dependent variable and the independent variable, the parameters of a tested oil sample are observed among multiple known oil sample points in a system database, thus constructing data tables $X=\{x_1, \ldots, x_p\}$ and $Y=\{y_1, \ldots, y_n\}$ for the independent variable and the dependent variable, inputting the spectral band of the oil sample being tested, including the ratio of reflection frequency and amplitude of the reflection energy so called DN value, and obtaining detection results by quantitative calculation by partial least squares regression inversion.

22. The lubricant oil analysis method according to claim 19, wherein a statistical and inferred regression algorithm, the partial least squares method is adopted to analyze the statistical relationship between the dependent variable and the independent variable, partial least squares regression is performed on X and Y respectively based on the index of the oil sample being tested and the corresponding spectral band thereof, and based on the extent to which the independent variable component is able to explain the dependent variable component, that is, the extent to which the detection index corresponds to a known spectral band, first components $t_1$ and $u_1$ are extracted; and partial least squares regression is conducted for the regression of X relative to $t_1$ and Y relative to $u_1$, respectively; if the regression equation is satisfied, the algorithm terminates; otherwise, the residual information after X has been explained by $t_1$ and the residual information after Y has been explained by $u_1$ is used to extract a second round of components; with repeated iteration until a satisfactory accuracy is achieved, and the spectrum that is obtained includes the ratio of reflectivity and DN values; if m component $t_1, t_2, \ldots, t_m$ bands are ultimately extracted from spectrum X, in the partial least squares regression, one elemental component index $y_k$ is regressed against $t_1, t_2, \ldots, t_m$ wavebands in an inversion calculation to obtain a certain elemental index of the oil sample being tested.

23. The lubricant oil analysis method based according to claim 20, wherein a mathematical expression of a stepwise process of partial least squares method comprises the steps of:
  establishing a residual information matrix $E_0$ and a detected oil sample component matrix $F_0$, where $E_0$ is a standardized independent variable matrix, each row is a series of component indices, and each column denotes a set of spectral band variables corresponding to the detected element indices; $F_0$ is a dependent variable matrix; similarly to $E_0$, each row is a series of component indices, and each column denotes a set of spectral band variables corresponding to the detected element indices; where data normalization consists of subtracting the mean of each spectral band, and then dividing by the standard deviation of each spectral band;
  solving for the eigenvector $w_1$ corresponding to the maximum eigenvalue of the matrix $E_0^T F_0 F_0^T E_1$ to obtain a component score vector $\hat{t}_1 = E_0 w_1$ and a residual information matrix $E_1 = E_0 - \hat{t}_1 a_1^T$, wherein $a_1 = E_0^T \hat{t}_1 / \|\hat{t}_1\|^2$; solving for the eigenvector $w_2$ corresponding to the maximum eigenvalue of the matrix $E_1^T F_0 F_0^T E_1$ to obtain a component score vector $\hat{t}_2 = E_0 w_2$ and the residual information matrix $E_2 = E_1 - \hat{t}_2 a_2^T$, wherein $a_2 = E_1^T \hat{t}_2 / \|\hat{t}_2\|^2$;
  repeating the above steps to the $m^{th}$ step, solving for the eigenvector $w_m$ corresponding to the maximum eigenvalue of the matrix $E_{m-1}^T F_0 F_0^T E_{m-1}$ to obtain a component score vector $\hat{t}_m = E_{m-1} w_m$;

based on cross validity, determining that a total of m components $t_1, t_2, \ldots, t_m$ have been extracted to obtain a prediction model;

solving the common least squares regression equation for $F_0$ on $t_1, t_2, \ldots, t_m$:

$$F_0 = \hat{t}_1 \beta_1^T + \hat{t}_2 \beta_2^T + \ldots + \hat{t}_m \beta_m^T + F_m$$

wherein $\beta_1$, $\beta_2$, and $\beta_m$ denote the weighting parameters of the $1^{st}$, $2^{nd}$, and $m^{th}$ components, respectively, and Fm denotes the residual information matrix after extracting m components;

if data tables X and Y are subjected to m components ultimately extracted for X, substituting $t_k = w_{k1}^* x_1 + w_{k2}^* x_2 + \ldots + w_{kn}^* x_n (k=1, 2, \ldots, m)$ into $Y = t_1 \beta_1 + t_2 \beta_2 + \ldots + t_m \beta_m$ to obtain a partial least squares method regression equation of p dependent variables:

$$y_j = a_{j1} x_1 + a_{j2} x_2 + \ldots + a_{jn} x_n (j=1,2,\ldots,p)$$

such that $w_h^* = (w_{h1}^*, w_{h2}^*, \ldots, w_{hn}^*)^T$ satisfies $\hat{t}_h = E_0 w_h^*$ $w_h^* = \Pi_{j=1}^{h-1} (I - w_j a_j^T) w_h$.

24. The lubricant oil analysis method according to claim 21, further comprising an objective function characterized in that:

$$\min \| y_j - \delta_1 a_{j1} x_1 - \ldots - \delta_k a_{jk} x_k - \delta_n a_{jn} x_n \| + \left\| tr\left(w_h^{*T} E_0 w_h^*\right) - tr\left(\hat{t}_h E_0 \hat{t}_h^T\right) \right\|,$$

wherein $$\delta_k = \cfrac{1}{1 + \left| \cfrac{L_{DN}(\lambda_k) - \overline{L}_{DN}}{\overline{L}_{DN}} \right|},$$

$$j = 1, 2, \ldots, p$$

with $L_{DN}(\lambda_k)$ being the $k^{th}$ band radiance value and $\overline{L}_{DN}$ being the band average radiance value, and with the constraint condition being: $a_{jl} > 0, \ldots, a_{jk} > 0, a_{jn} > 0$.

25. The lubricant oil analysis method according to claim 21, wherein the preset spectral band is in the range of from 400 nm to 1,000 nm.

* * * * *